(12) United States Patent
Zegarelli

(10) Patent No.: US 12,156,773 B2
(45) Date of Patent: Dec. 3, 2024

(54) METHODS OF MAKING AN ORAL APPLIANCE

(71) Applicant: Emanate Biomedical, Inc., New York, NY (US)

(72) Inventor: Peter John Zegarelli, Sleepy Hollow, NY (US)

(73) Assignee: Emanate Biomedical, Inc., Larchmont, NY (US)

( * ) Notice: Subject to any disclaimer, the term of this patent is extended or adjusted under 35 U.S.C. 154(b) by 0 days.

(21) Appl. No.: 17/963,602

(22) Filed: Oct. 11, 2022

(65) Prior Publication Data

US 2023/0037613 A1 Feb. 9, 2023

Related U.S. Application Data

(62) Division of application No. 15/895,554, filed on Feb. 13, 2018, now abandoned.

(51) Int. Cl.
| | | |
|---|---|---|
| *A61C 19/06* | (2006.01) | |
| *A61J 7/00* | (2006.01) | |
| *A61M 31/00* | (2006.01) | |
| *B29C 64/124* | (2017.01) | |
| *B29L 31/00* | (2006.01) | |
| *B33Y 10/00* | (2015.01) | |
| *B33Y 80/00* | (2015.01) | |

(52) U.S. Cl.
CPC ............ *A61C 19/063* (2013.01); *A61J 7/0092* (2013.01); *A61M 31/002* (2013.01); *B29C 64/124* (2017.08); *B33Y 10/00* (2014.12); *B33Y 80/00* (2014.12); *A61M 2207/00* (2013.01); *A61M 2210/0625* (2013.01); *B29L 2031/753* (2013.01)

(58) Field of Classification Search
CPC ...... B29C 64/124; B33Y 10/00; A61C 19/063
See application file for complete search history.

(56) References Cited

U.S. PATENT DOCUMENTS

| 3,234,942 A | 2/1966 | Simor |
|---|---|---|
| 3,339,547 A | 9/1967 | Drabowski |

(Continued)

FOREIGN PATENT DOCUMENTS

| EP | 1570803 | 9/2005 |
|---|---|---|
| MX | 2006006946 | 8/2006 |

(Continued)

OTHER PUBLICATIONS

International Search Report and Written Opinion of the International Searching Authority (ISA/US) mailed Jul. 1, 2019 issued in Application No. PCT/US19/17223 filed on Feb. 8, 2019.

(Continued)

*Primary Examiner* — Jacob T Minskey
*Assistant Examiner* — Wayne K. Swier
(74) *Attorney, Agent, or Firm* — Sorell, Lenna & Schmidt, LLP

(57) ABSTRACT

An oral appliance and a method of making the oral appliance for delivering a medicament to an oral cavity are provided. The method comprises forming a non-porous material into a portion of the oral appliance; and applying a porous material to one or more discrete regions of the portion of the oral appliance to make the one or more discrete regions of the oral appliance porous thereby forming the oral appliance.

11 Claims, 15 Drawing Sheets

(56) References Cited

U.S. PATENT DOCUMENTS

| | | |
|---|---|---|
| 3,527,219 A | 9/1970 | Greenberg |
| 3,536,069 A | 10/1970 | Gores et al. |
| 3,624,909 A | 12/1971 | Greenberg |
| 3,705,585 A | 12/1972 | Saffro |
| RE28,667 E | 12/1975 | Gores et al. |
| 4,064,628 A | 12/1977 | Weitzman |
| 4,173,219 A | 11/1979 | Lentine |
| 4,173,505 A | 11/1979 | Jacobs |
| 4,430,013 A | 2/1984 | Kaufman |
| 4,676,752 A | 6/1987 | Lefkowitz |
| 5,085,585 A | 2/1992 | Zimble |
| 5,129,824 A | 7/1992 | Keller |
| RE34,196 E | 3/1993 | Munro |
| 5,234,342 A | 8/1993 | Fischer |
| 5,323,787 A | 6/1994 | Pratt |
| 5,326,685 A | 7/1994 | Gaglio et al. |
| 5,575,654 A | 11/1996 | Fontenot |
| 5,707,235 A | 1/1998 | Knutson |
| 5,711,935 A | 1/1998 | Hill |
| 5,732,715 A | 3/1998 | Jacobs et al. |
| 5,842,860 A | 12/1998 | Funt |
| 5,851,512 A | 12/1998 | Fischer |
| 5,895,218 A | 4/1999 | Quinn et al. |
| 5,895,249 A | 11/1999 | Fischer |
| 5,980,249 A | 11/1999 | Fontenot |
| 5,985,249 A | 11/1999 | Fischer |
| 6,030,213 A | 2/2000 | Trop |
| 6,126,443 A | 3/2000 | Burgio |
| 6,045,811 A | 4/2000 | Dirksing et al. |
| 6,210,162 B1 | 4/2001 | Chishti et al. |
| 6,217,606 B1 | 4/2001 | Portnoy et al. |
| 6,247,930 B1 | 6/2001 | Chiang et al. |
| 6,274,122 B1 | 8/2001 | McLaughlin |
| 6,276,935 B1 | 8/2001 | Funt |
| 6,319,510 B1 | 11/2001 | Yates |
| 6,386,869 B1 | 5/2002 | Zegarelli |
| 6,458,380 B1 | 10/2002 | Leaderman |
| 6,471,511 B1 | 10/2002 | Chishti et al. |
| 6,626,669 B2 | 9/2003 | Zegarelli |
| 6,638,496 B2 | 10/2003 | McLaughlin |
| 6,660,029 B2 | 12/2003 | VanSkiver et al. |
| 6,896,519 B2 | 5/2005 | Chen |
| 6,925,857 B2 | 8/2005 | Weber |
| 6,935,857 B1 | 8/2005 | Farrell |
| 6,966,773 B2 | 11/2005 | Keller |
| 6,984,128 B2 | 1/2006 | Breining et al. |
| 7,029,690 B1 | 4/2006 | Wehrli |
| 7,036,514 B2 | 5/2006 | Heck |
| 7,044,929 B2 | 5/2006 | VanSkiver |
| 7,055,530 B2 | 6/2006 | Husted |
| 7,059,858 B2 | 6/2006 | McLean |
| 7,063,532 B1 | 6/2006 | Jones et al. |
| 7,074,042 B2 | 7/2006 | Allred |
| 7,074,426 B2 | 7/2006 | Kochinke |
| 7,114,953 B1 | 10/2006 | Wagner |
| 7,134,874 B2 | 11/2006 | Chishti et al. |
| 7,160,111 B2 | 1/2007 | Baughman |
| 7,172,423 B2 | 2/2007 | Allred |
| 7,192,280 B2 | 3/2007 | Allred |
| 7,241,143 B2 | 7/2007 | Discko, Jr. et al. |
| 7,708,557 B2 | 5/2010 | Rubbert |
| 7,766,658 B2 | 8/2010 | Tricca et al. |
| 8,113,837 B2 | 2/2012 | Zegarelli |
| 8,172,569 B2 | 5/2012 | Matty |
| 8,505,541 B2 | 8/2013 | Bardach et al. |
| 8,585,406 B2 | 11/2013 | Zegarelli |
| 9,205,601 B2 | 12/2015 | De Simone et al. |
| 9,579,178 B2 | 2/2017 | Zegarelli |
| 9,649,182 B2 | 5/2017 | Zegarelli |
| 2002/0042038 A1 | 4/2002 | Miller et al. |
| 2003/0003421 A1 | 1/2003 | Bestenheider et al. |
| 2003/0205234 A1 | 11/2003 | Bardach et al. |
| 2003/0207227 A1 | 11/2003 | Abolfathi |
| 2004/0015327 A1 | 1/2004 | Sachdeva et al. |
| 2004/0110110 A1 | 6/2004 | Chishti et al. |
| 2004/0229185 A1 | 11/2004 | Knopp |
| 2004/0253562 A1 | 12/2004 | Knopp |
| 2005/0042210 A1 | 2/2005 | Akai |
| 2005/0055118 A1 | 3/2005 | Nikolskiy et al. |
| 2005/0070782 A1 | 3/2005 | Brodkin |
| 2005/0137109 A1 | 6/2005 | Quan et al. |
| 2005/0137110 A1 | 6/2005 | Scott et al. |
| 2005/0143274 A1 | 6/2005 | Ghosh et al. |
| 2006/0115782 A1 | 6/2006 | Li et al. |
| 2006/0115790 A1 | 6/2006 | Alon et al. |
| 2006/0199141 A1* | 9/2006 | Wen .................. A61C 3/00 433/24 |
| 2006/0275736 A1 | 12/2006 | Wen |
| 2007/0071693 A1 | 3/2007 | Kurihara et al. |
| 2007/0122360 A1 | 5/2007 | Oniki et al. |
| 2007/0207434 A1* | 9/2007 | Kuo .................. A61C 7/08 433/6 |
| 2008/0044797 A1 | 2/2008 | Bardach et al. |
| 2009/0117507 A1 | 5/2009 | Abolfathi et al. |
| 2009/0136893 A1 | 5/2009 | Zegarelli |
| 2009/0146344 A1 | 6/2009 | El-Siblani |
| 2009/0248184 A1 | 10/2009 | Steingart et al. |
| 2009/0269720 A1 | 10/2009 | O'Donnell |
| 2010/0086890 A1 | 4/2010 | Kuo |
| 2011/0136077 A1 | 6/2011 | De Moyer |
| 2012/0028221 A1 | 2/2012 | Williams |
| 2012/0214123 A1 | 8/2012 | Zegarelli |
| 2012/0276295 A1* | 11/2012 | Jahns .................. C04B 35/486 427/377 |
| 2013/0052613 A1 | 2/2013 | Chetiar et al. |
| 2013/0053613 A1* | 2/2013 | Chalabi .................. F23B 5/00 588/306 |
| 2016/0278902 A1 | 9/2016 | Zegarelli |
| 2017/0007386 A1 | 1/2017 | Mason et al. |
| 2017/0028178 A1 | 2/2017 | Skoda |
| 2017/0132393 A1 | 5/2017 | Natarajan et al. |
| 2017/0232300 A1 | 8/2017 | Tran et al. |

FOREIGN PATENT DOCUMENTS

| | | |
|---|---|---|
| WO | 2000 009036 | 2/2000 |
| WO | 2000 019928 | 4/2000 |
| WO | 2017197262 A1 | 11/2017 |

OTHER PUBLICATIONS

International Search Report and Written Opinion of the International Searching Authority (ISA/US) mailed Jun. 21, 2019 issued in Application No. PCT/US19/17225 filed on Feb. 8, 2019.

* cited by examiner

METHODS OF MAKING AN ORAL APPLIANCE

BACKGROUND

Medicaments may be delivered to patients by a variety of ways including oral, intravenous, intramuscular, inhalation, topical, rectal, subcutaneous or local routes of administration to treat the target site. The method of delivery chosen depends, among other things, upon the condition being treated, desired therapeutic concentration of the medicament and the duration of medicament concentration that must be maintained at the target site.

Recently, there has been considerable interest in delivering medicaments via the oral cavity (e.g., gums, buccal, and sublingual areas, etc.). Delivery to target sites of the oral cavity has several advantages. One advantage is that it allows localized treatment of the teeth, gums and other soft tissues. Another advantage is that the oral cavity has an extensive network of blood capillaries under the mucosa that is particularly suited to provide rapid and effective systemic absorption of systemic medicaments.

Oral appliances that allow non-invasive delivery of medicaments have been developed that have a reservoir to hold liquid medicaments to be delivered. These oral appliances are available in universal sizes to generically fit adults or are custom made for a precise fit to the teeth and gums of a particular individual patient. To whiten teeth, these oral appliances are becoming increasingly popular as over-the-counter tooth whitening systems or as part of a treatment plan from dental professionals. These oral appliances have a non-porous exterior.

It would be beneficial to provide oral appliances that can be easily manufactured, have discrete porous regions to control delivery of a medicament to a target tissue site within the oral cavity, and be effective at protecting against contamination or dilution of the medicament by saliva or other oral fluids. It would also be beneficial to provide oral appliances that can be easily loaded with medicament at these discrete porous regions to control delivery of a medicament at the target tissue site within the oral cavity.

SUMMARY

New oral appliances are provided that can be easily manufactured that have discrete porous regions to control delivery of the medicament to a target tissue site (e.g., gums, gum line, teeth, etc.) within the oral cavity. In some embodiments, new oral appliances are provided that can be easily loaded with medicament at these discrete porous regions to control delivery of the medicament at the target tissue site within the oral cavity. In some embodiments, new oral appliances are provided where the entire oral appliance can be easily loaded with medicament and the medicament will be absorbed by the porous material disposed at discrete regions of the oral appliance to control delivery of the medicament at the target tissue site within the oral cavity.

In some embodiments, the oral appliance is entirely porous and has a porous exterior. However, there are discrete regions that are non-porous.

In some embodiments, there is a method of making an oral appliance for delivering a medicament to an oral cavity, the method comprising forming a non-porous material into a portion of the oral appliance; and applying a porous material to one or more discrete regions of the portion of the oral appliance to make the one or more discrete regions of the oral appliance porous thereby forming the oral appliance.

In some embodiments, there is a method of making an oral appliance for delivering a medicament to an oral cavity, the method comprising forming a non-porous material into a portion of the oral appliance; and applying a porous material to one or more discrete regions of the portion of the oral appliance to make the one or more discrete regions of the oral appliance porous thereby forming the oral appliance.

In some embodiments, there is a method of making an oral appliance for delivering a medicament to an oral cavity, the method comprising forming a porous material containing a medicament into the oral appliance; and applying a non-porous material to one or more discrete regions of the porous material to make the one or more discrete regions of the oral appliance non-porous.

In some embodiments, there is a method of making an oral appliance for delivering a medicament to an oral cavity, the method comprising forming a porous material containing a medicament into the oral appliance; and applying an agent to reduce porosity to one or more discrete regions of the porous material to make the one or more discrete regions of the oral appliance non-porous.

In some embodiments, there is an oral appliance for delivering a medicament to at least a portion of teeth and/or soft tissue areas inside an oral cavity, the oral appliance comprising a porous material containing a medicament and a non-porous material disposed on or in one or more discrete regions of the porous material to make the one or more discrete regions of the oral appliance non-porous, the oral appliance being formed to fit contours of at least the portion of the teeth and/or soft tissue areas inside the oral cavity and being configured for holding the medicament in contact with at least the portion of the teeth and/or soft tissue areas inside the oral cavity to deliver the medicament thereto.

In some embodiments, there is a method of making an oral appliance for delivering a medicament to an oral cavity, the method comprising forming a porous material into a portion of the oral appliance; and applying a non-porous material to one or more discrete regions of the portion of the oral appliance to make the one or more discrete regions of the oral appliance non-porous thereby forming the oral appliance.

In some embodiments, there is a method of making an oral appliance, the method comprising: providing a carrier and an optically transparent member having a build surface, the carrier and the build surface defining a build region therebetween; filling the build region with a polymerizable liquid; irradiating the build region through the optically transparent member to form a solid polymer from the polymerizable liquid while concurrently advancing the carrier away from the build surface to form the oral appliance from the solid polymer, wherein the oral appliance has discrete regions of porous material.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings.

Figure 1:
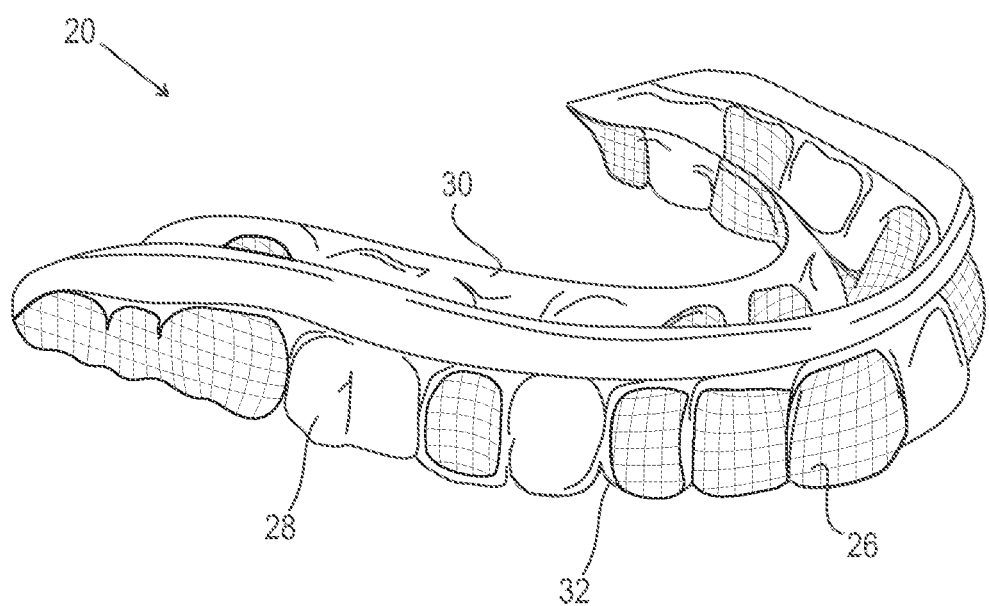
FIG. 1 illustrates a perspective view of an embodiment of an oral appliance covering the upper teeth and/or soft tissues of a patient. The oral appliance comprises a porous material containing a medicament and a non-porous material disposed on or in one or more discrete regions of the porous material to make the one or more discrete regions of the oral appliance non-porous.

It is to be understood that the figures are not drawn to scale. Further, the relationship between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a medicament" includes one, two, three or more medicaments.

The term "porous" as used herein, refers to a material which is permeable such that fluids are movable therethrough by way of pores or other passages. An example of a porous material is a hydrogel material, a cellulosic material, concrete, ceramics, foams, sponges and derivatives thereof. The porous material may be the result of using a low or high molecular weight polymer. In some embodiments, the polymer may be porous as it is printed at a low density on the oral appliance and/or substrate, or is printed in a geometric pattern, either as a specific structure or a randomized structure.

The term "non-porous" as used herein, refers to a material which is impermeable such that fluids cannot move through the material. The non-porous material may be the result of using a low or high molecular weight polymer. In some embodiments, the polymer may be non-porous as it is printed at a high density on the oral appliance and/or substrate in a solid form with no structural spacing to hold medicaments, as described above.

The term "hydrogel" or "hydrogels" refer to a broad class of polymeric materials, that may be natural or synthetic, which have an affinity for an aqueous medium (e.g., a medicament), and are able to absorb large amounts of the aqueous medium, but which do not normally dissolve in the aqueous medium.

The term "medicament" as used herein, is generally meant to refer to any substance that alters the physiology of a patient. The term "medicament" may be used interchangeably herein with the terms "medicine", "drug", "therapeutic agent", "therapeutically effective amount", or "active pharmaceutical ingredient". It will be understood that a "medicament formulation" may include more than one therapeutic agent, wherein exemplary combinations of therapeutic agents include a combination of two or more medicaments.

The terms, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

The term "localized" delivery includes delivery where one or more medicaments contact the tooth and/or soft tissue areas, for example, the gingival margins of the teeth or a region inside of the mouth such as the palate, or in close proximity thereto.

The term "targeted delivery" includes delivery of one or more medicaments at the target site as needed for treatment of the disease or condition including cosmetic applications, for example, whitening teeth or removing stains. In some embodiments, the oral appliance can be used to deliver medicament to the soft tissue of the inside of the mouth, including but not limited to any soft tissue adjacent or between the teeth, including but not limited to the papilla, tissue of the upper and lower dental arches, marginal gingiva, gingival sulcus, inter-dental gingiva, gingival gum structure on lingual and buccal surfaces up to and including the muco-gingival junction and/or the palate and/or the floor of the mouth. In various embodiments, the soft tissue area includes the muco-buccal folds, hard and soft palates, the tongue, lining mucosa, and/or attached gingival tissue.

The term "custom fit" as used herein, refers to an oral appliance that is specifically made via molding and/or 3D printing, to correspond to at least a portion of a tooth, a selected number of teeth, all of the teeth and/or soft tissues found in the mouth of a specific individual patient. A custom fit oral appliance is not a generic device which is then heated or otherwise manipulated by a consumer, inserted into their mouth by themselves and then molded by that consumer to fit their own mouth. The patient image is the result of an action upon that particular individual by another person whereas the consumer is acting upon himself/herself by manually manipulating the generic material.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

Oral Appliance

Unlike orthodontic appliances, the present oral appliance is not designed to move teeth and is not an orthodontic appliance. Therefore, a plurality of oral appliances will be configured to fit the teeth in the same position as was imaged within the oral appliance. The teeth position will not change. However, the medicament disposed in or on the oral appliance will be in the same or different areas at different stages of the treatment regimen with a variety of oral appliances. Thus, kits containing a plurality of oral appliances can be provided with different treatment plans. For example, as the patient condition improves, each oral appliance will have a decreasing amount of medicament or the medicament can change as the treatment progresses.

In various embodiments, the oral appliance is monolithic or a single piece and the interior surface custom fit and formed to fit contours of the teeth and/or soft tissue areas inside the oral cavity of a patient in need of treatment. Unlike other devices in the market, the device of the present application has the medicament as part of the device and in some embodiments, the medicament is not removable from it except by diffusion in the mouth. In certain embodiments, the oral appliance comprises, consists essentially of or consists of one, two, three, four, five or more oral appliances.

In some embodiments, oral appliances include, but are not limited to, oral trays, oral holders, oral covers, or the like that are designed to be placed within the oral cavity. The interior surface and/or exterior surface of the oral appliance contains a medicament disposed inside the porous portion of the polymer of the oral appliance and the medicament can be disposed anywhere within or on the oral appliance as part of this monolithic device. In some embodiments, the exterior surface of the oral appliance is porous and allows medicament to be released to adjacent teeth and/or soft or hard tissue, or into the mouth in general.

Numerous different oral appliances can be made by the methods of the present application, including custom fit oral appliances that correspond to a digital scan taken from the patient's mouth or impression molds. Custom fit oral appliances are generally described in U.S. Pat. No. 9,649,182, to Peter J. Zegarelli, filed Jun. 18, 2015. The entire disclosure of this patent is herein incorporated by reference into the present disclosure.

The oral appliance when worn allows the interior and/or exterior surface of the oral appliance to be adjacent to the teeth and/or gums or other tissue in the oral cavity. In some embodiments, the oral appliance receives one or more teeth including one or more molars, premolars, incisors, cuspids, tooth implant, or combinations or portions thereof.

The contact of the oral appliance with the tissue, when the oral appliance contains medicament in the porous regions, will allow medicament to be released from the oral appliance to the target tissue areas in the oral cavity (e.g., gum, gum line, teeth, etc.) at the desired regions adjacent to the porous regions of the oral appliance. In this way, targeted therapy can be directed at the desired regions in the oral cavity. By providing an oral appliance with porous regions and non-porous regions, medicament release can be controlled to adjacent tissue or confined to those regions adjacent to the non-porous material without dilution or contamination by oral fluids such as saliva or releasing the medicaments onto non-targeted areas of the mouth with sometimes deleterious effects.

In some embodiments, the oral appliance is predominantly porous (at least 51% or more) and non-porous material is coated on the oral appliance at discrete regions to make these discrete regions non-porous. In this way, medicament loading of the oral appliance and medicament release from the oral appliance is controlled as medicament will be released from the porous material at discrete regions and can target specific tissues in the oral cavity.

It will be understood that the medicament can be mixed with the polymer before, during or after the manufacture of the oral appliance.

In some embodiments, the oral appliance is made from a porous material that contains the medicament, and an agent that reduces porosity is applied to one or more discrete regions of the porous material to make the one or more discrete regions of the oral appliance non-porous. For example, a crosslinking agent can be used to reduce porosity of a porous oral appliance and make that region where the crosslinking agent is applied to non-porous to reduce or eliminate medicament release from that region.

In some embodiments, the oral appliance can be made by controlling the print density of the polymer during 3D printing or additive manufacturing. For example, the same polymer can be printed (e.g., using the same print head) at a density of, for example, 0.25 g/cm$^3$ to 0.5 g/cm$^3$ at discrete regions to form the porous regions of the oral appliance and at a higher density for example, 0.8 g/cm$^3$ to 1.5 g/cm$^3$ to make the oral appliance non-porous at discrete regions.

In some embodiments, the oral appliance can be made by controlling the density of the polymer during 3D printing or additive manufacturing. For example, different polymers can be printed using two or more print heads, each print head having a different polymer. A high density polymer can be used (e.g., 50,000 MW) and printed at discrete regions to form the non-porous regions of the oral appliance and another print head can use a low density polymer (e.g., 5,000 MW) to make the oral appliance porous at discrete regions.

It will be understood that the oral appliance with discrete portions of the porous material and with discrete portions of non-porous material can be monolithic or a single piece having the same or different material. This type of oral appliance, in some embodiments, does not contain a porous insert after the oral appliance is made. Such porous inserts are described in U.S. Pat. No. 9,579,178, filed Jul. 12, 2013 to Peter J. Zegarelli. The entire disclosure of this patent is herein incorporated by reference into the present disclosure.

Referring to FIGS. 1-7, an oral appliance 20 is provided for delivering a medicament 22 to at least a portion of a tooth or teeth 24 and/or soft tissue areas inside an oral cavity, as shown in FIGS. 1-7. The appliance shown is a custom fit oral appliance, which can be formed to fit contours of and/or hold medicament in contact with at least a portion of the tooth or teeth and/or soft tissue areas, such as the gum 27 inside the oral cavity to deliver the medicament to these areas of one particular individual patient. The oral appliance can be constructed from a digital data set or a physical model representing at least a portion of or all of the teeth and/or soft tissue areas inside the oral cavity. All or portions of an exterior surface 32 of FIG. 1 can be porous as well to allow medicament to be released in the oral cavity including, for example, the gingival margins, interior of the lip and the palates, floor of the mouth, the sublingual veins, the tongue, buccal mucosas and labial mucosas.

The oral appliance 20 comprises a porous material 26. The porous material can be made from a polymer material such as a hydrogel material or other material that will make all or portions of the oral appliance porous. The porous material can be mixed with the medicament or the medicament can be added to the porous material after manufacture. Shown in FIG. 1 is the oral appliance having the porous material disposed at discrete regions of the oral appliance. For example, the oral appliance is predominantly porous (at least 51% or more) and non-porous material is coated on the oral appliance at discrete regions to make these discrete regions of non-porous material 28. The porous material allows the medicament to be saturated within the polymer.

The porous material comprises from about 60% to about 99% by weight of the oral appliance. In some embodiments, the porous material comprises from about 65% to about 95%, from about 70% to about 90%, from about 75% to about 85%, or from about 80 to about 82% by weight of the oral appliance. In some embodiments, the porous material comprises from about 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99% by weight of the oral appliance. The porous material can cover a part or a portion of a tooth, as shown as 26a in FIGS. 2-4. The porous material can cover a part or a portion of a tooth or teeth and/or soft oral tissue such that those particular portions selected can be the only portions treated by the medicament.

The oral appliance comprises a non-porous material 28. The non-porous material is disposed on or in one or more discrete regions of the porous material to make the one or more discrete regions of the oral appliance non-porous. In some embodiments, the medicament is not added before or after manufacture to the non-porous regions of the oral appliance. The non-porous material reduces medicament release from the oral appliance. The non-porous material can be a cross-linked polymer. For example, the entire oral appliance can be made from a porous material and a polymer crosslinking agent can be applied to the oral appliance at discrete regions of the oral appliance to make these discrete regions non-porous.

Figure 1A:
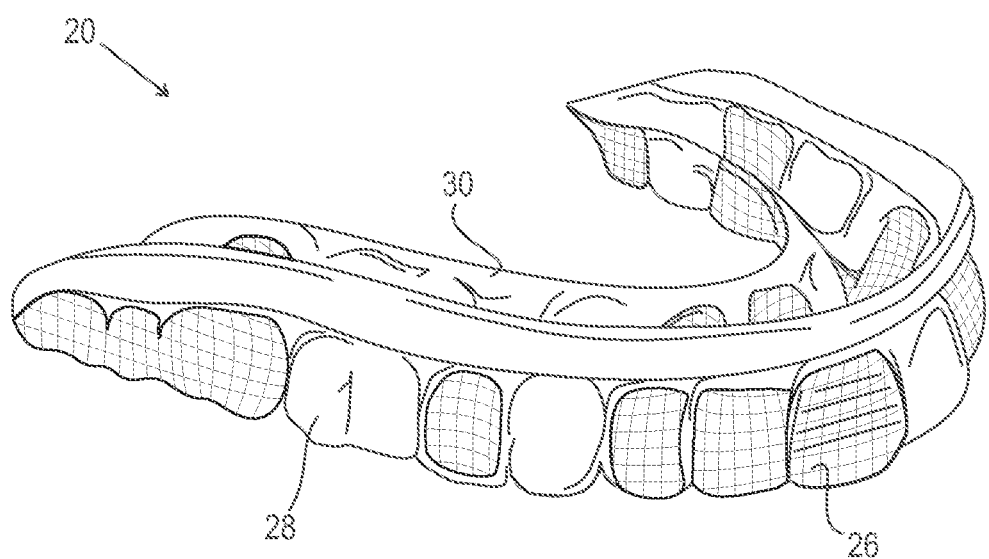
FIG. 1A illustrates a perspective view of an embodiment of an oral appliance, where the porous material comprises a polymer that is printed at a high density at discrete regions to form non-porous regions of the oral appliance and printed at a low density at discrete regions of the oral appliance to make porous regions of the oral appliance.

FIG. 1A illustrates another embodiment of the oral appliance 20 made by controlling the print density of the polymer during 3D printing or additive manufacturing. For example, the same polymer can be printed (e.g., using the same print head) by programming the computer to have the 3D printer print the polymer at a density of, for example, 0.25 g/cm$^3$ to 0.5 g/cm$^3$ at discrete regions to form the porous material regions 26 of the oral appliance, and the printer can be set to print the polymer at a higher density, for example, 0.8 g/cm$^3$ to 1.5 g/cm$^3$ to make the oral appliance non-porous at discrete regions with highly dense polymer printed to form the non-porous material 28 at discrete regions of the oral appliance.

Some printing densities of the polymer can be from about 0.25 g/cm$^3$, 0.3, 0.35, 0.4, 0.45, 0.5, 0.55, 0.6, 0.65, to about 0.7 g/cm$^3$ that can form the porous region of the oral appliance. This region can be saturated with medicament. The medicament can be mixed with the polymer before or during 3D printing, or can be added to the porous regions after printing.

Figure 1B:
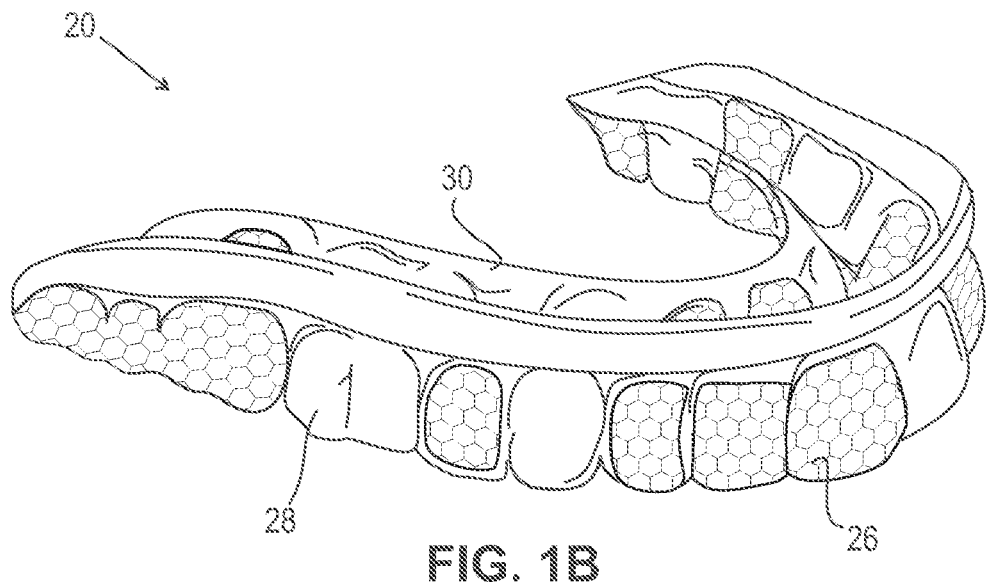
FIG. 1B illustrates a perspective view of an embodiment of the oral appliance, where the porous material comprises an open cell, lattice, honeycomb, or other random or geometric patterned configuration at discrete locations.
Figure 2:
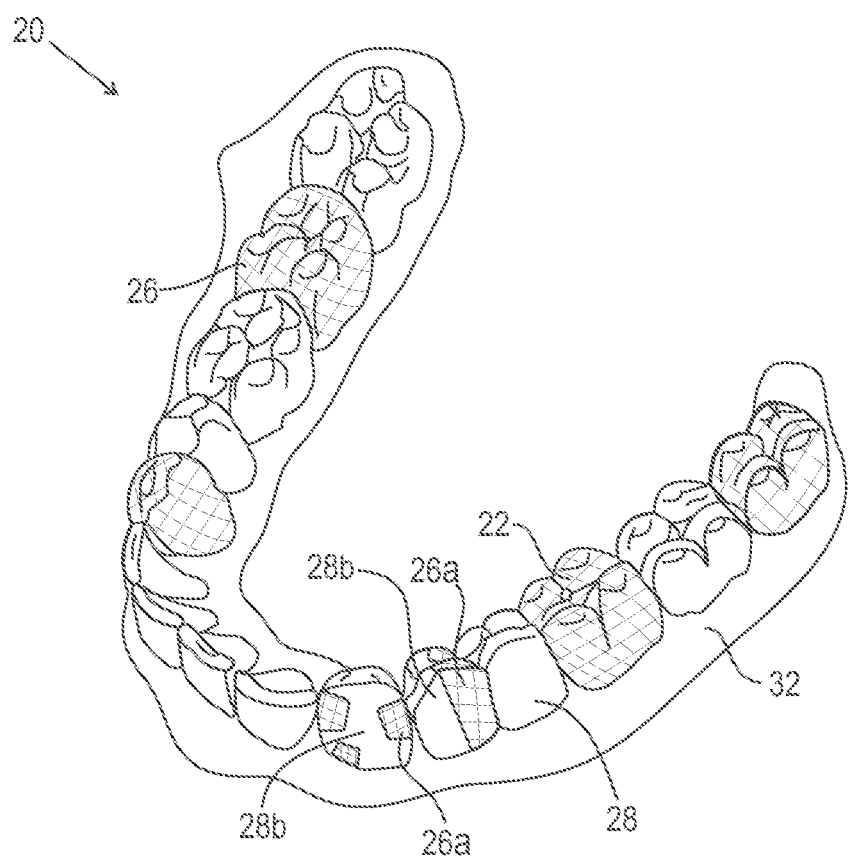
FIG. 2 illustrates a perspective view of the oral appliance of FIG. 1 covering the lower teeth and/or soft tissues of a patient.
Figure 3:
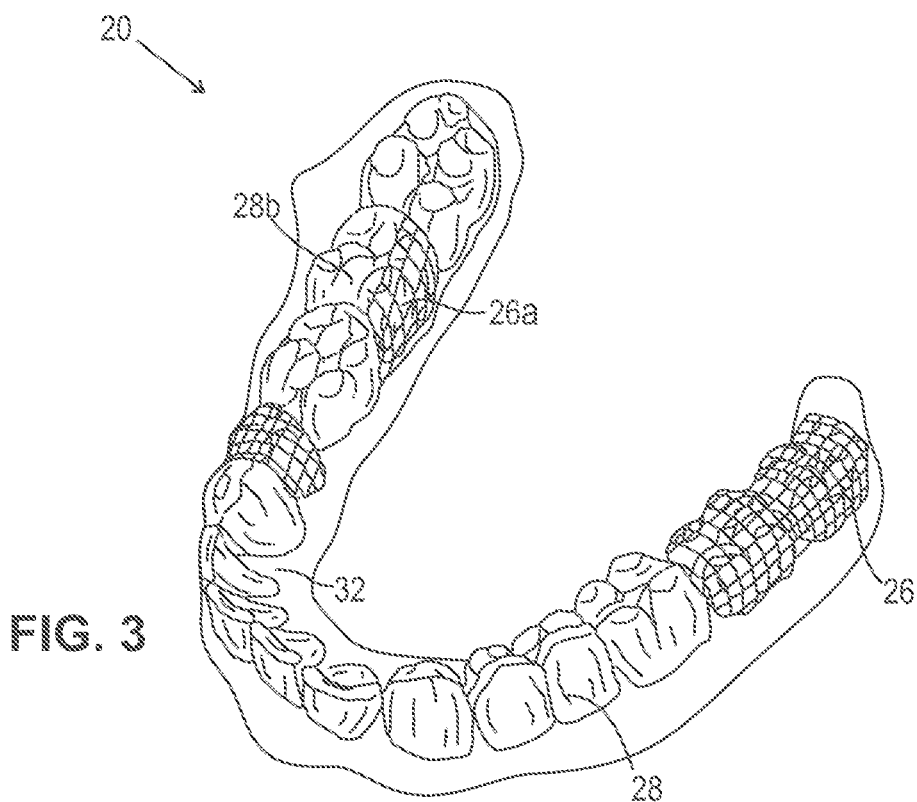
FIG. 3 illustrates a perspective view of the oral appliance of FIG. 1 covering the lower teeth and/or soft tissues of a patient.
Figure 4:
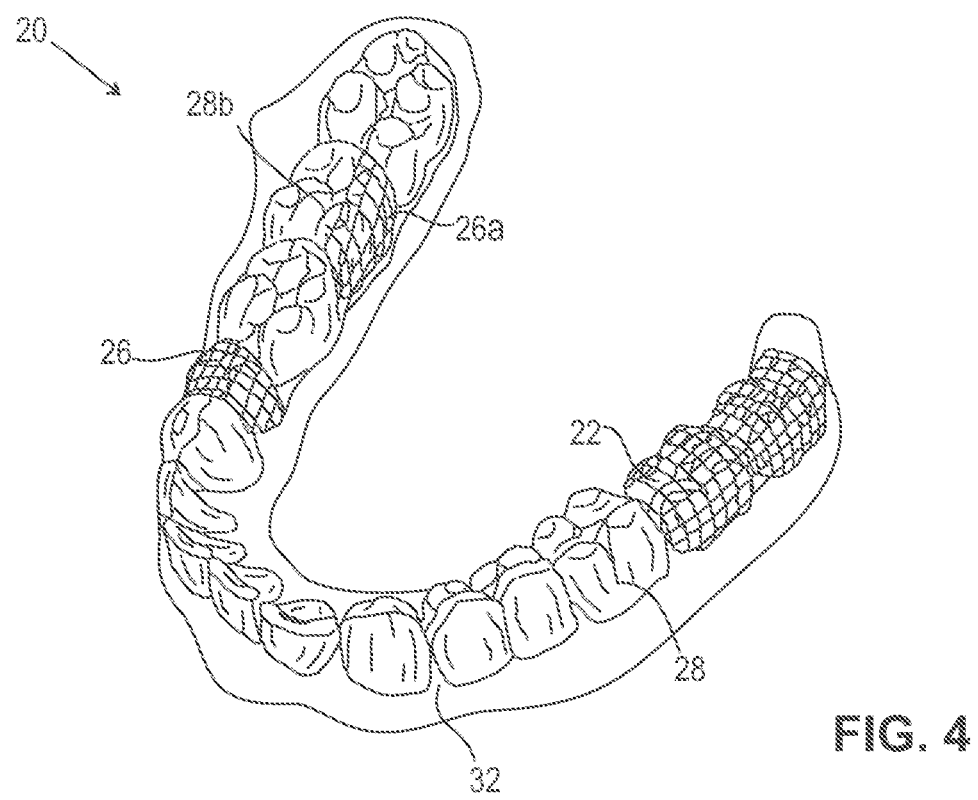
FIG. 4 illustrates a perspective view of the oral appliance of FIG. 1 covering the lower teeth and/or soft tissues of a patient.
Figure 5:
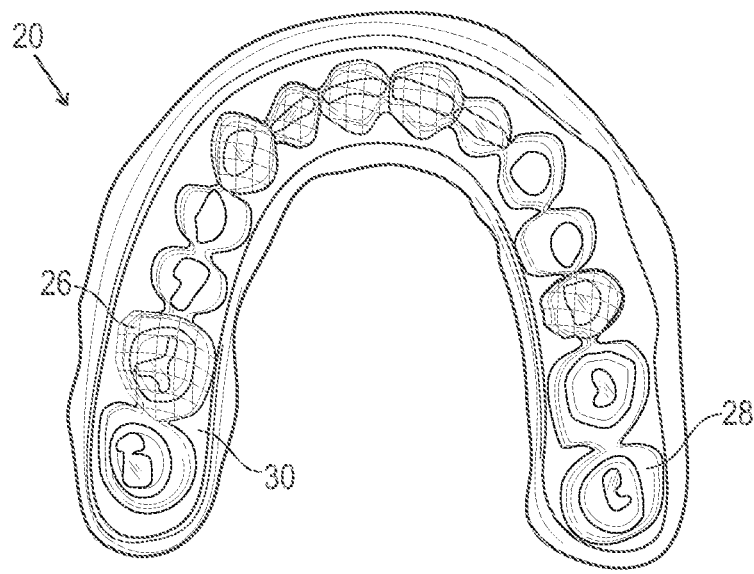
FIG. 5 illustrates a top view of the oral appliance of FIG. 1 covering the lower teeth and/or soft tissues of a patient.
Figure 6:
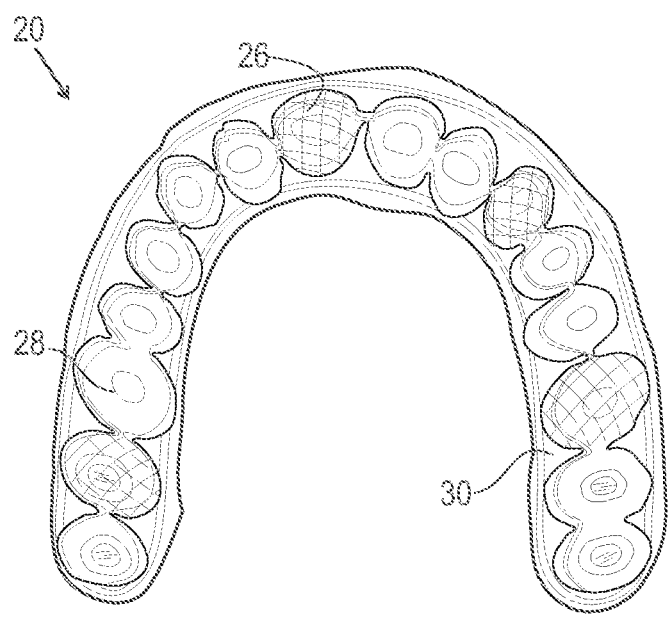
FIG. 6 illustrates a bottom view of the oral appliance of FIG. 1 covering the lower teeth and/or soft tissues of a patient.
Figure 7:
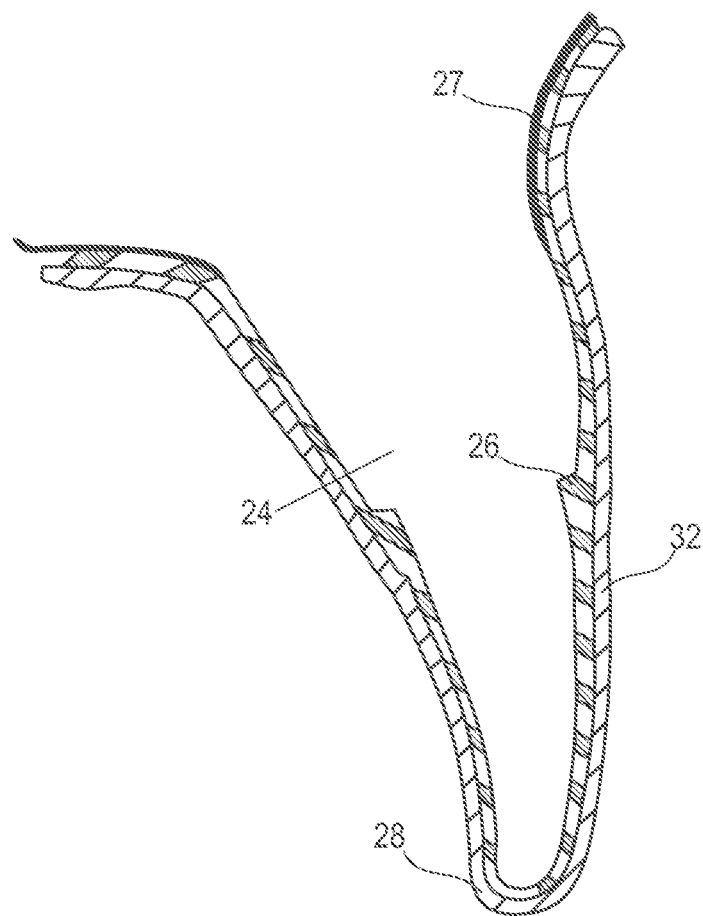
FIG. 7 illustrates a side cross sectional view of the oral appliance of FIG. 1 covering the teeth and/or soft tissues of a patient.

FIG. 1B illustrates another embodiment of the oral appliance 20 made by 3D printing or additive manufacturing. In some embodiments as shown in FIG. 1B, the non-porous material 28 does not contain portions of open cells, lattices or honeycombs. It is printed as a solid with no porosity and thereby no spacing to hold or absorb medicaments. These regions of the oral appliance will allow little or no medicament to contact the target tissue area in the mouth. In the embodiment shown, the oral appliance can have portions of open cells, lattices, honeycombs, or have sponge-like configurations as part of the oral appliance at discrete regions of it to target the areas to be treated. The entire oral appliance is made from one material and printed at one time. The porous material 26, or discrete regions of the oral appliance includes or is manufactured to include carbon foam, polymer(s), or a combination thereof. The foam can be a carbon foam lattice, such as carbon resin DPR 10 (Carbon 3D, Inc. C.A.).

The non-porous material comprises from about 0.25% to about 10% by weight of the oral appliance. In some embodiments, the non-porous material comprises from about 0.5% to about 8%, from about 1% to about 7%, from about 2% to about 6%, or from about 3% to about 5% by weight of the oral appliance. In some embodiments, the non-porous material comprises from about 0.25, 0.3, 0.35, 0.4, 0.45, 0.5, 0.55, 0.6, 0.65, 0.7, 0.75, 0.8, 0.85, 0.9, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, to about 99% by weight of the oral appliance.

The non-porous material is disposed on or in one or more discrete regions of the porous material such that the tooth, teeth and/or soft tissue areas that correspond to this region or regions is not treated with the medicament. In some embodiments, the non-porous material can cover a part or portion of a tooth, as shown as 28b in FIGS. 2-4. In some embodiments, the non-porous material is a coating that is applied to discrete regions of the oral appliance and/or porous material. Such coating for example can be a cross-linking agent, which allows crosslinking of the porous polymer to reduce or eliminate medicament release from the oral appliance and/or confine medicament to a portion of the teeth and/or gum that is adjacent to the non-porous region of the oral appliance.

In some embodiments, the non-porous material can be coated on the oral appliance at discrete regions of it and the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the medicament from the oral appliance. In some embodiments, the range of the coating on the oral appliance ranges from about 5 microns to about 250 microns or 5 microns to about 200 microns to delay release of the medicament from the oral appliance.

The oral appliance includes an interior surface 30 and an exterior surface 32. The interior and exterior surfaces are defined by the porous and non-porous materials of the oral appliance. The interior surface is custom formed to fit contours of at least a portion of the teeth and/or soft tissue areas inside the oral cavity and is configured for holding the medicament in contact with at least the portion of the teeth and/or soft tissue areas inside the oral cavity to deliver the medicament thereto.

In some embodiments, the non-porous material is the structural backbone of the oral appliance and is present throughout the oral appliance to give it form, shape and structural integrity. The porous material parts of the oral appliance are strategically placed about the oral appliance in order to deliver medicaments to those areas to be treated. These areas can be either internal or external to the oral appliance.

The oral appliance may have a porosity suitable for release of the liquid medicament upon application of the liquid medicament to the oral appliance. The porosity of the oral appliance ranges from about 1 micron to about 750 microns, from about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740 to about 750 microns. In some embodiments, the oral appliance has a porosity ranging from about 100 microns to about 500 microns.

The oral appliance has a thickness of from about 0.06 inches to about 0.2 inches. In some embodiments, the oral appliance has a uniform thickness or a non-uniform thickness ranging from about 0.06, 0.07, 0.08, 0.09, 0.10, 0.11, 0.12, 0.13, 0.14, 0.15, 0.16, 0.17, 0.18, 0.19, to about 0.2 inches. The oral appliance can have a uniform or non-uniform thickness of about 0.2 to about 0.5 inches. In some embodiments, the oral appliance comprises a semi-solid construction.

Oral Appliance Materials

The oral appliance can be made of any materials that can hold and release the medicament. In various embodiments, the material from which the oral appliance can be made from includes swellable polymers, such as, for example hydrogels, gels, polymer brushes or combinations thereof.

In some embodiments, suitable polymers for use to make the oral appliance include, for example, polyacrylates, polyamide-imide, phenolic, nylon, nitrile resins, petroleum resins, fluoropolymers, copolyvidones (copovidones), epoxy, melamine-formaldehyde, diallyl phthalate, acetal, coumarone-indene, acrylics, acrylonitrile-butadiene-styrene, alkyds, cellulosics, polybutylene, polycarbonate, polycaprolactones, polyethylene, polyimides, polyphenylene oxide, polypropylene, polystyrene, polyurethanes, polyvinyl acetates, polyvinyl chloride, poly(vinyl alcohol-co ethylene), styrene acrylonitrile, sulfone polymers, saturated or unsaturated polyesters or combinations thereof.

In some embodiments, the polymer comprises, consists essentially of or consists of an amount from about 5% to about 100% by weight, from about 5%, 10%, 15%, 20%, 25%, 30%, 35%, 40%, 45%, 50%, 55%, 60%, 65%, 70%, 75%, 80%, 85%, 90%, 95% to about 100% by weight, from about 10% to about 15% by weight, from about 15% to about 20% by weight, from about 20% to about 25% by weight, from about 25% to about 30% by weight, from about 30% to about 35% by weight, from about 35% to about 40% by weight, from about 40% to about 45% by weight, from about 45% to about 50% by weight, from about 50% to about 55% by weight, from about 55% to about 60% by weight, from about 60% to about 65% by weight, from about 65% to about 70% by weight, from about 70% to about 75% by weight, from about 75% to about 80% by weight, from about 80% to about 85% by weight, from about 85% to about 90% by weight, from about 90% to about 95% by weight, or from about 95% to about 100% by weight of the oral appliance. In some embodiments, the oral appliance is substantially all polymer from about 80% to about 99.9% by weight. The medicament comprises, consists essentially of or consists of an amount from about 0.01% to about 50%, from about 0.1% to about 20% by weight, from about 0.5% to about 10%, or from about 1% to about 7% by weight of the oral appliance.

In various embodiments, the molecular weight of the polymer can be a wide range of values. The average molecular weight of the polymer can be from about 1000 to about 10,000,000 g/mol; or about 1,000 to about 1,000,000; or about 5,000 to about 500,000; or about 10,000 to about 100,000; or about 20,000 to about 50,000 g/mol.

In some embodiments, when the oral appliance is made from one polymer, the density of the polymer can vary such that the non-porous and porous regions are formed in the oral appliance from a single material.

In some embodiments, when different molecular weight polymers are used, the polymer can be dense and have a higher molecular weight such that the polymer is non-porous. In some embodiments, the polymer can be less dense and have a lower molecular weight such that the polymer is porous. In some embodiments, the oral appliance can be made from multiple polymers, as described above. The multiple polymers can have the same or different densities. The polymers can have an average molecular weight of from about 1000 to about 10,000,000 g/mol; or about 1,000 to about 1,000,000; or about 5,000 to about 500,000; or about 10,000 to about 100,000; or about 20,000 to about 50,000 g/mol.

The polymer can have a modulus of elasticity (Young's modulus) in the range of about $1 \times 10^{-2}$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

The polymer may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the polymer can comprise a hydrogel that is or is not infused with at least one medicament. Suitable hydrogels for use in the oral appliance, include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (for example, PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrolidone), acrylates such as poly(2-hydroxy ethyl methacrylate) and copolymers of acrylates with N-vinyl pyrolidone, N-vinyl lactams, polyacrylonitrile or combinations thereof.

In some embodiments, cross-linking agents used to make the porous material non-porous include, but are not limited to, glutaraldehyde, formaldehyde, epoxy, compounds, dialdehyde, sodium borate/boric acid, glyoxal, oxidized dextrins, epichlorohydrin, endogen polyamine spermidine, oxidized alginate, zinc, borax, ethylene glycol dimethacrylate (EGDMA), N, N'-methylenebisacrylamide, derivatives of ethylene glycol di(meth)acrylate, derivatives of methylenebisacrylamide, formaldehyde-free crosslinking agent including N-(1-Hydroxy-2,2-dimethoxyethyl)acrylamide, or a combination thereof.

In some embodiments, it may be difficult for the medicament to move in and out of the oral appliance. In some embodiments, a porosity reducing agent such as a crosslinking agent is used to generate a non-porous region on the polymer oral appliance.

In some embodiments, the oral appliance can be transparent so that a user can see the teeth. The oral appliance may be disposable and sterilizable. In various embodiments, one or more components of the oral appliance is sterilized by radiation in a terminal sterilization step in the final packaging. Terminal sterilization of a product provides greater assurance of sterility than from processes such as an aseptic process, which require individual product components to be sterilized separately and the final package assembled in a sterile environment. Other methods may also be used to sterilize one or more components of the oral appliance, including, but not limited to, E-beam radiation, gamma radiation, gas sterilization, such as, for example, with ethylene oxide or steam sterilization Medicaments The oral appliance contains one or more medicaments coated, layered on it, impregnated within it at the same or different areas to form a monolithic oral appliance. In various embodiments, some areas of the polymer material of the oral appliance do not contain one or more medicaments, and the polymer material may function to hold or lock a portion of the polymer material in place so that other portions of the polymer material can contact the appropriate target site. Thus, in some embodiments, the polymer material may contain one or more medicaments disposed in or on it throughout the whole polymer material of the oral appliance. In other embodiments, one or more portions of the oral appliance do not contain any medicament disposed in or on it (e.g., the non-porous regions of the oral appliance). The term "medicament" as used herein is generally meant to refer to any substance that alters the physiology of a patient. The term "medicament" may be used interchangeably herein with the terms "medicine", "drug" "therapeutic agent", "therapeutically effective amount", or "active pharmaceutical ingredient". It will be understood that a "medicament formulation" may include more than one therapeutic agent, wherein exemplary combinations of therapeutic agents include a combination of two or more medicaments. The medicament can also include cells, where the device (e.g., oral appliance) can be seeded with the cells, for example, gingival cells or gingival tissue, bone cells, cartilage cells, bone tissue so that the device can repair or replace tissue in the treatment area.

The medicament may be in powder, liquid, solid, solution, or suspension (e.g., gel) form and disposed on or impregnated in the oral appliance. This may occur during manufacture of the oral appliance or it may occur after the oral appliance is made. For example, on the core polymer material of the oral appliance, the medicament may be layered by solution or suspension layering or powder layering techniques. In solution or suspension layering, the medicament and any inactive ingredients (excipients, binders, etc.) are suspended or dissolved in water or an organic solvent. The resulting liquid is sprayed onto the outside of the oral appliance to make the polymer material have the desired potency. Solution or suspension layering may be conducted using a wide variety of process techniques, for example, by fluidized bed, Wurster bottom spray techniques, or the like. When the desired potency has been achieved, the polymer material is dried to the desired residual moisture content. Powdered layering involves the application of a dry powder to the oral appliance. The powder may contain the drug, or may include excipients such as a binder, flow aid, inert filler, and the like. In the powder layering technique, a pharmaceutically acceptable liquid, which may be water, organic solvent, with or without a binder and/or excipients, is applied to the oral appliance while applying the dry powder until the desired potency is achieved. When the desired potency has been achieved, the oral appliance may be dried to the desired moisture content.

In various embodiments, the medicament is in liquid form and is capable of diffusing through and within the oral appliance comprising a polymer material. In various embodiments, the liquid medicament may flow or diffuse from one portion of the oral appliance to another portion. In some embodiments, the liquid medicament may not flow or diffuse within the oral appliance. In some embodiments, the liquid medicament is confined within the regions of the oral appliance corresponding to the treatment area. The liquid medicament is not capable of flowing or diffusing into the non-porous regions of the oral appliance. In some embodiments, the liquid medicament may flow or diffuse into the non-porous regions; however the medicament cannot easily flow or diffuse out of the non-porous regions.

Examples of medicaments include, but are not limited to, anti-inflammatory agents, anti-infective agents (e.g., antiviral, antibacterial, antifungal agents, etc.), tissue and bone growth factors, pain management medication (e.g., analgesics, anesthetics, etc.) antineoplastic agents, tooth whitening agents, breath fresheners, anticalculus agents, antineoplastic agents, oral dermatologics, selective H-2 antagonists, anticaries agents, nutrients, vitamins, minerals, herbal products, opioids, or mixtures thereof.

In various embodiments, the oral appliance may contain more than one medicament. However, in another embodiment, combination therapy will involve use of a single, safe and effective amounts of the medicament. For example, the method may further comprise subsequently administering one or more additional oral appliances, each containing a medicament that is different from the medicament contained in the earlier oral appliance. In this way, a series of customized treatment regimens can be provided to the patient. This provides for a "mix and match" medicament regimen with dose adjustment capability and provides the added advantage of allowing the health professional complete control to administer only those medicaments at the desired strength believed to be appropriate for the disease or condition being treated to a particular individual.

In some embodiments, one or more oral appliances can be administered to a patient to provide opioid or other addictive drug therapy to treat pain or other conditions. The medications in these cases can be more closely monitored due to the specific number of appliances produced and be more difficult to extract from the appliances to be sold or otherwise abused. Additionally, since, like fingerprints, no two mouths are the same and the appliances will be manufactured to a specific individual, it will be difficult if not impossible for another individual to use them. Also, if the appliances are sold by the individual they are made for, they will be easily traceable back to that individual not only by the anatomy of the appliance but also by having the appliances marked with a numbering identification system (e.g., unique number sequences, patient identification number, letters, bar code, etc.) to further identify the oral appliance for monitoring and identification. This will be a method for biometrically administering and following the usage of drugs and making sure they are being administered properly.

Therefore, in some embodiments, the oral appliance can be a biometric oral appliance because it is custom fit to the individual patient and the individual patient can be more closely monitored, the individual patient's medicament monitored according to the prescription, and any illicit sale of the oral appliance can also be monitored as the oral appliance will be biometrically specific to that patient as the oral cavity provides a unique finger print for that patient and their treatment. For example, if the medicament in the oral appliance for the first patient or a plurality of oral appliances for the first patient is an opioid or other abused drug, the oral appliance is specific to the first patient's mouth and not another patient's mouth, and the medicament cannot be transferred to another patient as the oral appliance is unique and specific to the first patient's mouth. It will not properly function in the other patient's mouth. In this way, compliance and transfer of the oral appliance can be tracked.

In some embodiments, the oral appliance can have an opioid, or other addictive or abused drug (e.g. medicament) disposed in discrete porous portions or throughout the entire oral appliance. The opioid, or other addictive or abused drug can include, but is not limited to, 1-phenylcyclohexylamine, 1-piperidinocyclohexanecarbonitrile, alfentanil, alphacetylmethadol, alphaprodine, alprazolam, amobarbital, amphetamine, anileridine, apomorphine, aprobarbital, barbital, barbituric acid derivative, bemidone, benzoylecgonine, benzphetamine, betacetylmethadol, betaprodine, bezitramide, bromazepam, buprenorphine, butabarbital, butalbital, butorphanol, camazepam, cathine, chloral, chlordiazepoxide, clobazam, clonazepam, clorazepate, clotiazepam, cloxazolam, cocaine, codeine, chlorphentermine, delorazepam, dexfenfluramine, dextromoramide, dextropropoxyphen, dezocine, diazepam, diethylpropion, difenoxin, dihydrocodeine, dihydromorphine, dioxaphentyl butyrate, dipanone, diphenoxylate, diprenorphine, ecgonine, enadoline, eptazocine, estazolam, ethoheptazine, ethyl loflazepate, ethylmorphine, etorphine, femproponex, fencamfamin, fenfluramine, fentanyl, fludiazepam, flunitrazepam, flurazepam, glutethimide, halazepam, haloxazolam, hexalgon, hydrocodone, hydromorphone, isomethadone, hydrocodone, ketamine, ketazolam, ketobemidone, levanone, levoalphacetylmethadol, levomethadone, levomethadyl acetate, levomethorphan, levorphanol, lofentanil, loperamide, loprazolam, lorazepam, lormetazepam, lysergic acid, lysergic acid amide, mazindol, medazepam, mefenorex, meperidine, meptazinol, metazocine, methadone, methamphetamine, methohexital, methotrimeprazine, methyldihydromorphinone, methylphenidate, methylphenobarbital, metopon, morphine, nabilone, nalbuphine, nalbupine, nalorphine, narceine, nefopam, nicomorphine, nimetazepam, nitrazepam, nordiazepam, normethadone, normorphine, oxazepam, oxazolam, oxycodone, oxymorphone, pentazocine, pentobarbital, phenadoxone, phenazocine, phencyclidine, phendimetrazine, phenmetrazine, pheneridine, piminodine, prodilidine, properidine, propoxyphene, propofol, cocaine, racemethorphan, racemorphan, racemoramide, remifentanil, secobarbital, sufentanil, talbutal, thebaine, thiamylal, thiopental, tramadol, trimeperidine, and vinbarbital.

In addition to the above, the following scheduled drugs or abused drugs may also be incorporated into the oral appliance, including, but not limited to, allobarbitone, alprazolam, eszopiclone, ramelteon, amylobarbitone, aprobarbital, barbital, barbitone, benzphetamine, brallobarbital, bromazepam, brotizolam, buspirone, butalbital, butobarbitone, butorphanol, camazepam, captodiame, carbromal, carfentanil, carpipramine, cathine, chloral, chloral betaine, chloral hydrate, chloralose, chlordiazepoxide, chlorhexadol, chlormethiazole edisylate, chlormezanone, cinolazepam, clobazam, potassium clorazepate, clotiazepam, cloxazolam, cyclobarbitone, delorazepam, dexfenfluramine, diazepam, diethylpropion, difebarbamate, difenoxin, dronabinol, enciprazine, estazolam, ethyl loflazepate, etizolam, febarbamate, fencamfamin, fenfluramine, fenproporex, fluanisone, fludiazepam, flunitraam, flunitrazepam, flurazepam, flutoprazepam, gepirone, glutethimide, halazepam, haloxazolam, hexobarbitone, ibomal, ipsapirone, ketamine, ketazolam, loprazolam mesylate, lorazepam, lormetazepam, mazindol, mebutamate, medazepam, mefenorex, mephobarbital, meprobamate, metaclazepam, methaqualone, methohexital, methylpentynol, methylphenobarbital, midazolam, milazolam, morphine, nimetazepam, nitrazepam, nordiazepam, oxazepam, oxazolam, paraldehyde, pemoline, pentabarbitone, pentazocine, pentobarbital, phencyclidine, phenobarbital, phendimetrazine, phenmetrazine, phenprobamate, phentermine, phenyacetone, pinazepam, pipradol, prazepam, proxibarbal, pseudoephedrine, ephedrine, epinephrine, anabolic steroids (e.g., testosterone, or syhtestic anabolic steroids) human growth hormone, quazepam, quinalbaritone, secobarbital, secbutobarbitone, sibutramine, temazepam, tetrazepam, triazolam, triclofos, zalepan, zaleplon, zolazepam, zolpidem, and zopiclone. Certain compounds described herein may exist in particular geometric or stereoisomeric forms.

In some embodiments, the amount of opioid, or other addictive or abused drug disposed in the carrier can be in an amount of from about 0.1% to about 30%, from about 1% to about 20%, from about 1% to about 10% or from about 1% to 5% of the oral appliance. The amount of opioid, or other addictive or abused drug disposed in the carrier can be in an amount of from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29 to about 30% of the oral appliance. For example, a first oral appliance can be made specific or custom fit for a patient. The oral appliance can have porous and non-porous regions, the medicament can be in the porous and/or non-porous regions, for example, 5% oxycodone for pain based on the total weight of the oral appliance or polymer used to make the oral appliance. A second oral appliance can be made for that patient with the same or less amount of oxycodone, for example 2.5% oxycodone for pain based on the total weight of the oral appliance or polymer used to make the oral appliance. The prescriber will be able to taper the patient off of the oxycodone. Further, the patient will not be able to transfer the oral appliance as it will not properly function on other patients as the oral cavity is unique and the oral appliance can be tracked like a finger print. In this way, illegal use and sale of the opioid drug, additive drug or abused drug can be reduced or eliminated.

The amount of medicament contained within the oral appliance, will vary widely depending on the effective dosage required and rate of release from the polymer material and the length of the desired delivery interval. The dosage administered to the patient can be single or multiple doses and will vary depending upon a variety of factors, including the agent's pharmacokinetic properties, patient conditions and characteristics (sex, age, body weight, health, size, etc.), extent of symptoms, concurrent treatments, frequency of treatment and the effect desired. These factors can readily be determined by those of ordinary skill in the art.

In various embodiments, the polymer material of the oral appliance is designed to release the medicament as a bolus dose of the medicament, a single dose of the medicament, or multiple doses of the medicament all preloaded with a specific dosage at the manufacturing facility.

In some embodiments, the medicament described herein is in the oral appliance in an amount of from about 0.01, 0.02, 0.03, 0.04, 0.05, 0.06, 0.07, 0.08, 0.09, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to about 50% by weight of the oral appliance.

The oral appliance may comprise a safe and effective amount of one or more whitening agents such as bleaching agents or abrasive agents. Generally the level of the bleaching agent is dependent on the available oxygen or chlorine respectively that the molecule is configured for providing to bleach the stain. The bleaching agent may be present at levels from about 0.1% to about 20%, in another embodiment from about 0.5% to about 9% and in another embodiment from about 3% to about 8%, and in yet another embodiment from about 4% to about 6%, by weight of the bleaching agent composition.

In some embodiments, when the medicament is in liquid form, the polymer oral appliance is submerged in the liquid medicament. The polymer oral appliance will then absorb the liquid medicament into the porous material of the oral appliance. In some embodiments, the medicament and the polymer material are mixed together and the mixture is made into the oral appliance. In some embodiments, the oral appliance has a non-porous coating disposed on selected areas of the oral appliance that is impenetrable by the liquid medicament. In some embodiments, some portions of the oral appliance comprise non-porous materials that are impenetrable by the medicament.

In some embodiments, the medicament can be disposed anywhere in or on the interior or exterior surface of the oral appliance adjacent to the gum and/or other soft tissue areas of the oral cavity including the front, back, occlusal surfaces of one or more teeth. Some portions of teeth that do not require the medicament are sealed with the non-porous material which can be a coating, cross-linked with porosity reducing agent or comprise non-porous material such that the medicament cannot penetrate said portions. In some embodiments, the medicament may be disposed in or may enter the non-porous region. However, the medicament disposed in the non-porous region will not release the medicament or will release the medicament at a reduced rate.

In some embodiments, the medicament may enter the non-porous regions but the medicament will release slowly from these regions. For example, the medicament can be disposed at discrete non-porous regions adjacent to the treatment area or uniformly disposed throughout the device. In this example, the medicament will not be released to other regions that do not correspond with the treatment area.

In some embodiments, the medicament may flow into the non-porous regions but the medicament in the non-porous regions will release the medicament at a slower rate than that of the porous regions. As the interior and/or exterior surface of the oral appliance contacts the oral cavity, the medicament is released from the polymer such that all or parts of the oral appliance will degrade over time by the action of enzymes, by hydrolytic action and/or by other similar mechanisms in the oral cavity. In various embodiments, the degradation can occur either at the surface of the oral appliance at discrete positions (heterogeneous or surface erosion) or uniformly throughout the oral appliance (homogeneous or bulk erosion). In some embodiments, all or discrete portions of the interior surface will degrade and release medicament at or near the target site in the oral cavity. The oral appliance will cover at least a portion of the teeth and or gums, by applying the device over axis to cover the area of the teeth and or gums, and the oral appliance will be adjacent to the gingival sulcus or other soft tissue or hard tissue areas, which will allow the medicament, if desired, to be released from the polymer to these areas.

Methods of Making the Oral Appliance

The oral appliance is custom made to fit a specific patient. The custom made oral appliance may be prepared by a dental care professional including, but not limited to a dentist, oral surgeon, medical doctor, or manufacturer. The oral appliance can be made from an impression mold, or by using an analog or digital image capturing device. The oral appliance disclosed herein is not a boil and bite prefabricated device or a stock tray which can be manipulated by the consumer himself/herself with fingers to shape it against the teeth and gums. The oral appliance disclosed herein is custom fit, disposable, and monolithic that is pre-loaded with medicament in or on at least a portion of the porous interior and/or porous exterior surfaces of the appliance and can deliver medicaments. The medicament can be pre-loaded as part of the oral appliance or infused into the polymer of the oral appliance after the oral appliance is made.

The processes described herein can produce oral appliances with a variety of different properties. Hence in some embodiments the oral appliances are rigid; in other embodiments the products are flexible or resilient. In some embodiments, the oral appliances are a solid; in other embodiments, the oral appliances are a gel such as a hydrogel or have layers of such. In some embodiments, the oral appliances have a shape memory (that is, return substantially to a previous shape after being deformed, so long as they are not deformed to the point of structural failure).

Figure 13:
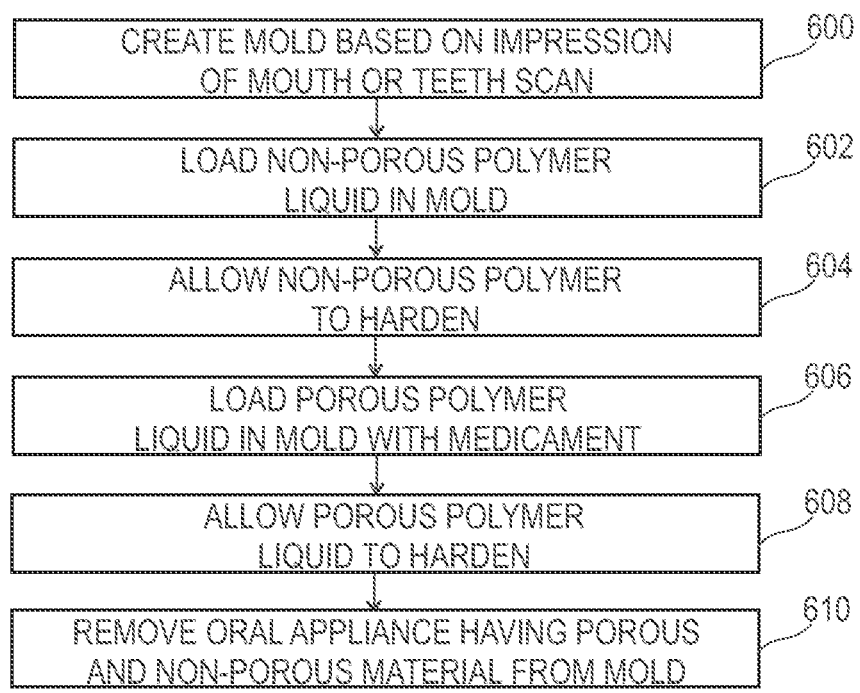
FIG. 13 is a flow chart illustrating one embodiment where the oral appliance is made by molding a non-porous polymer in a mold and then overmolding the porous material on the non-porous material to form the oral appliance.

Referring to FIG. 13, it shows a flow chart illustrating one embodiment where the oral appliance is made by molding a non-porous polymer in a mold and then overmolding the porous material on the non-porous material to form the oral appliance. In this process, a mold 600 of the patient's oral cavity is made from a digital scan of the mouth or impressions taken from the mouth. In step 602 a non-porous polymer is loaded. The polymer is allowed to harden in the mold in step 604. A porous polymer material that can be in liquid form is loaded with medicament and loaded in the mold in step 606. The porous polymer material can be a low molecular weight polymer in liquid form. In some embodiments, the porous polymer material can be overmolded on the non-porous polymer material. In some embodiments, the non-porous polymer material is a high molecular weight polymer that has a different glass transition temperature than the porous polymer material. The porous polymer material is allowed to harden on the non-porous polymer material in step 608 and the oral appliance with non-porous and porous regions with or without medicament is removed from the mold in 610.

3D Printing of Oral Appliance

Figure 8:
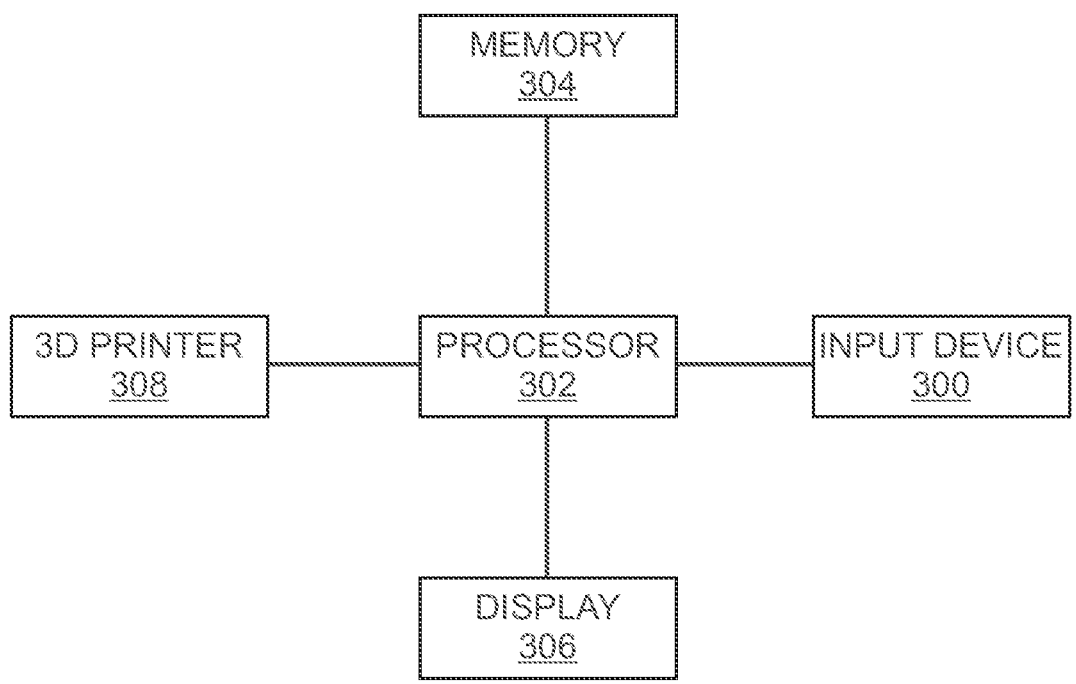
FIG. 8 is a block diagram of one embodiment of components to a computer-implemented system for producing an oral appliance by 3D printing or additive manufacturing.

In one embodiment, a computer-implemented system for producing an oral appliance by 3D printing or additive manufacturing is provided, as shown in FIG. 8. In this embodiment, an input device or scanner 300 is used to scan the oral cavity of and thus generate a digital record of the patient's mouth. The scanner can be an MRI scanner, a CT scanner, a PET scanner, a digital scanner, an X-Ray machine, or an intra-oral scanner, magnetic resonance imaging (MRI) scanner, coordinate measuring machine, destructive scanner or ultrasound scanner for example. In various embodiments, the scanner can scan the patient's teeth, soft tissue, or both to obtain a digital data set of the teeth and/or soft tissue areas inside the mouth from which is generated. The digital data can be stored in a database, such as for example a computer that has a processor 302, which sends the digital data to its memory 304 and/or can display it in a virtual 3D image display 306 of the processor. The database and/or processor can comprise an input device (e.g., keyboard, touch screen, voice activation, etc.) to allow a user to enter, display, edit, and/or transmit data. The input device can control the print heads being used, the print density of the printer head, the type of polymer being used, and whether one, two, or more print heads with different polymer weights to make the porous and/or non-porous material is used. The processor comprises logic to execute one or more instructions to carry instructions to the computer system (e.g., transmit instructions to a 3D printer 308, etc.). The logic for executing instructions may be encoded in one or more tangible media for execution by the processor. For example, the processor may execute codes stored in a computer-readable medium such as the memory. The computer-readable medium may be, for example, electronic (e.g., RAM (random access memory), ROM (read-only memory), EPROM (erasable programmable read-only memory)), magnetic, optical (e.g., CD (compact disc), DVD (digital video disc)), electromagnetic, semiconductor technology, or any other suitable medium.

In various embodiments, an authorized user can input, edit data and approve or prescribe a treatment plan. This can be displayed at the user interface of the computer processor and/or another treating computer networked with the computer processor. Although the components of the system of FIG. 8 are shown as separate, they may be combined in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general purpose computer (or other processor-controlled device) executing a program stored on an article of manufacture (e.g., recording medium or other memory units) to produce the functionality referred to herein may be utilized to implement the illustrated embodiments. It also will be understood that a plurality of computers or servers can be used to allow the system to be a network based system having a plurality of computers linked to each other over the network or Internet or the plurality of computers can be connected to each other to transmit, edit, and receive data via cloud computers.

The computer (e.g., memory, processor, storage component, etc.) may be accessed by authorized users. Authorized users may include at least one dentist or dental specialist, dental hygienist, oral surgeon, physician, surgeon, nurse, patient, and/or health care provider, manufacturer, etc.

The term "processing device" as used herein is intended to include any processor, such as, for example, one that includes a CPU (central processing unit) and/or other forms of processing circuitry. Further, the term "processing device" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the display device(s), input device(s), cursor control device(s), signal generation device(s), etc., can be collectively referred to as an "input/output interface," and is intended to include one or more mechanisms for inputting data to the processing device(s), and one or more mechanisms for providing results associated with the processing device(s).

Input/output or I/O devices including but not limited to keyboards (e.g., alpha-numeric input device(s), display device(s), and the like) can be coupled to the system either directly (such as via bus) or through intervening input/output controllers (omitted for clarity).

In an integrated circuit implementation of one or more embodiments of the disclosure, multiple identical die are typically fabricated in a repeated pattern on a surface of a semiconductor wafer. Each such die may include a device described herein, and may include other structures and/or circuits. The individual dies are cut or diced from the wafer, then packaged as integrated circuits. One skilled in the art would know how to dice wafers and package die to produce integrated circuits. Any of the exemplary circuits or method illustrated in the accompanying figures, or portions thereof, may be part of an integrated circuit. Integrated circuits so manufactured are considered part of this specification. Suitable 3D printing technology is described in U.S. Pat. No. 9,649,182, to Peter J. Zegarelli, filed Jun. 18, 2015. The entire disclosure of this patent is herein incorporated by reference into the present disclosure.

Figure 9:
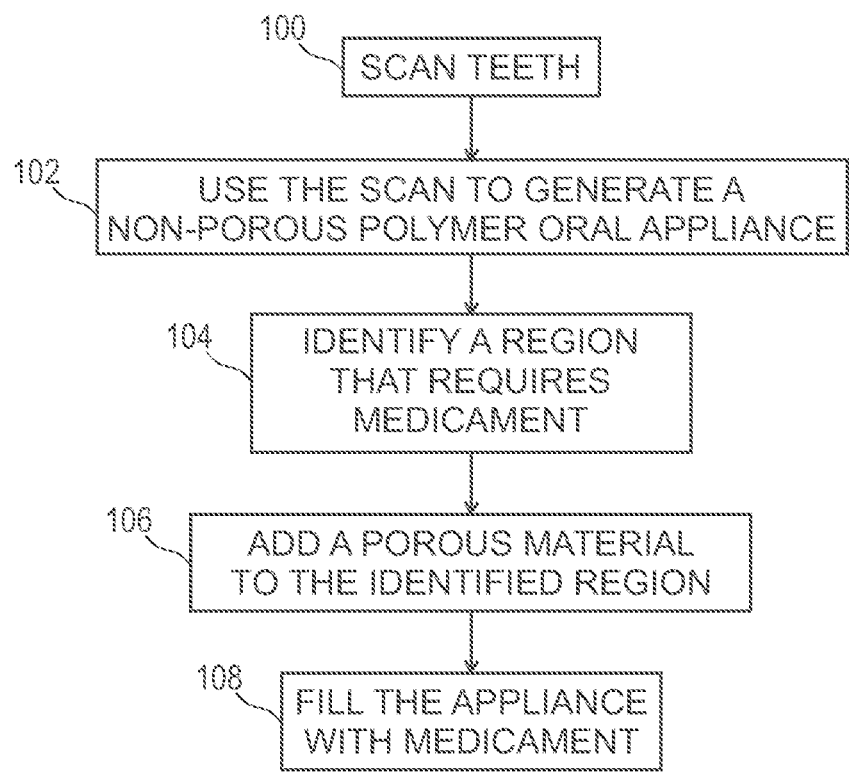
FIG. 9 is a flow chart illustrating one embodiment of the computer-implemented system and steps that the computer performs to produce a non-porous polymer oral appliance. The oral appliance also comprises discrete regions made from a porous material that is filled with the liquid medicament.

In some embodiments, a method of manufacturing an oral appliance is provided, as shown in FIG. 9. First, a patient's teeth are scanned (100) into a set of digital data, which shows the layout of the patient's teeth. The scanned image (the scan) is then used to generate a non-porous polymer oral appliance that contours the patient's teeth (102). Simultaneously or at a later time, the dental practitioner identifies a region in the patient's teeth that requires the medicament (104). A porous material is then added to this identified region (106). The porous material can be coated onto the oral appliance so that these identified regions are penetrated by the medicament. The oral appliance is then filled with medicament (108). The oral appliance can be filled with a liquid medicament via submerging the oral appliance into the liquid medicament.

Discrete regions of the oral appliance are porous such that when the oral appliance is submerged in the liquid medicament, it can absorb the liquid medicament. In some embodiments, the time period of absorption can be from about 1 minute to about 1 day, from about 5 minutes to about 10 minutes, from about 10 minutes to about 30 minutes, from about 30 minutes to about 1 hour, from about 1 hour to about 3 hours, from about 3 hours to 6 hours, from about 6 hours to about 12 hours, or from about 12 hours to about 24 hours.

Figure 10:
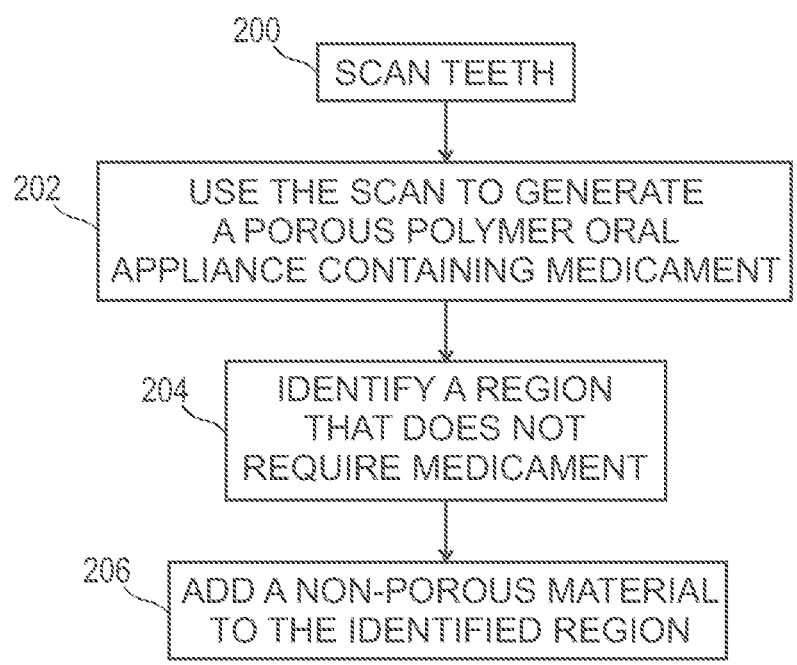
FIG. 10 is a flow chart illustrating one embodiment of the computer-implemented system and steps that the computer performs to produce a porous polymer oral appliance comprising the medicament. The oral appliance also comprises discrete regions made from a non-porous material.

In some embodiments, a method of manufacturing a polymer oral appliance is provided, as shown in FIG. 10. First, a patient's teeth are scanned (200) into a set of digital data, which creates an image showing the layout of the patient's teeth. The scanned image (the scan) is used to generate a porous polymer oral appliance that contours the patient's teeth (202). In some embodiments, the porous polymer oral appliance is generated through additive manufacturing such that the oral appliance is made with the medicament infused in the polymer porous material of the oral appliance. Simultaneously or at a later time, the dental practitioner identifies a region in the patient's teeth that does not require the medicament (204). A non-porous material is then added to the identified region (206). The non-porous material can be coated onto the oral appliance so that these identified regions are impenetrable by the medicament.

In some embodiments, the dental practitioner identifies the region that requires the medicament and the region that does not require the medicament. The region that requires the medicament is made with porous material infused with medicament and the region that does not require the medicament is made with non-porous materials.

In some embodiments, the medicament is infused within the polymer before the polymer is formed into the oral appliance. In some embodiments, the oral appliance is immersed in the liquid medicament and absorbs the liquid medicament into the polymer. The non-porous portions cannot absorb the medicament and the medicament cannot diffuse into the non-porous portions of the oral appliance.

In some embodiments, a polymerase inhibitor is added to the polymer to make the polymer porous. In some embodiments, a pore forming agent can be added to the polymer including but not limited to MgO (e.g., 1 wt. %), mPEG, propylene glycol, mannitol, trehalose, TBO-Ac, Span-65, Span-85, pluronic F127, sorbitol, xylitol, isomalt, erithritol, cyclodextrin, maltodextrin, pluronic F68, CaCl, dextran, dextran sulphate, dextran phosphate, hydroxypropylcellulose, ethylcellulose, PEG 1500, PEG 400, PEG 3350, acetyl tributyl citrate, butyl benzyl phthalate, butyl phthalyl butyl glycolate, dibutyl phthalate, dibutyl sebacate, diethyl phthalate, diethylene glycol dibenzoate, dipropylene glycol, dipropylene glycol dibenzoate, ethyl phthalyl ethyl glycolate, ethyl-p-toluene sulfonamide, hexylene glycol, methyl phthalyl ethyl glycolate, polyoxyethylene aryl ether and tributoxyethyl phthalate or combinations thereof. In some embodiments, a porogen can be added to the polymer and subsequently, the porogen can be leached with water to obtain a porous structure or region. Water soluble particulates such as salt and/or sugar can be used as the porogen. Adding a porogen to the polymer allows the pore size and porosity of the polymer to be adequately controlled by particle size of the added salt and/or sugar, the salt/polymer ratio and/or the sugar/polymer ratio.

Figure 11:
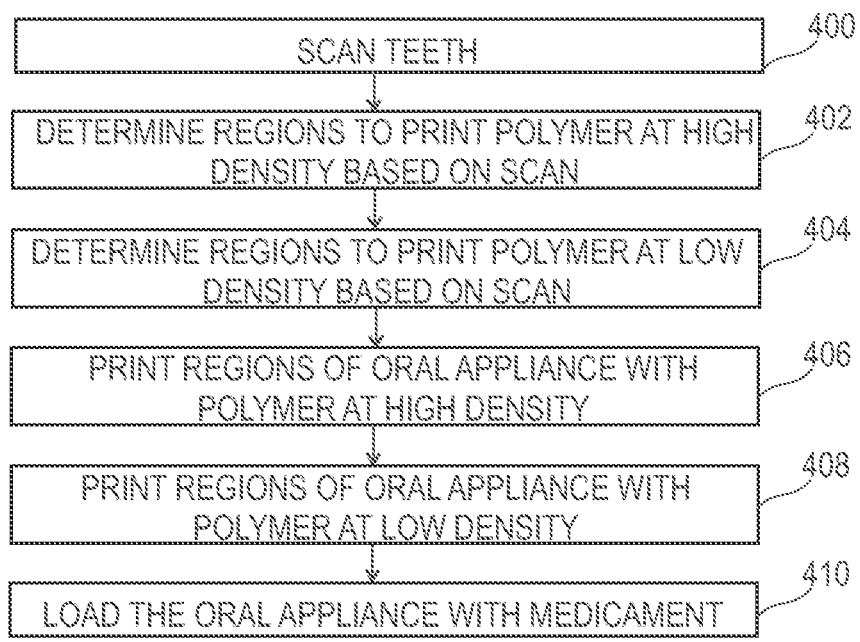
FIG. 11 is a flow chart illustrating one embodiment of the computer-implemented system and steps that the computer performs to produce the oral appliance, which is then loaded with medicament. The oral appliance comprises discrete regions made from porous and non-porous material, where the printer density of the polymer is controlled and areas of high density polymer printing are non-porous and areas of low density polymer printing are porous.

FIG. 11 is a flow chart illustrating one embodiment of the computer-implemented system that the computer performs to produce the oral appliance like that shown in FIG. 1A, which is then loaded with medicament.

In FIG. 11, when the oral appliance is made by 3D printing, the data from the scan of the teeth in step 400 is reviewed and the area for high density printing (non-porous region) of the oral appliance is determined in step 402. The data from the scan of the teeth in step 400 is reviewed and the area for low density printing (porous region) of the oral appliance is determined in step 404. Data is sent to the printer, which can be instructed by the computer to print the polymer at different densities so that one polymer material can be used to make the oral appliance. The 3D printer can be instructed to print polymer in a high density amount at discrete regions of the oral appliance in step 406 based on the scan, which will be the non-porous region of the oral appliance. The printer can be instructed and will then print a low density amount of polymer on the oral appliance in step 408 based on the scan to make discrete porous regions of the oral appliance. In some embodiments, the high density regions and the low density regions can be printed or manufactured either in separate steps, simultaneously or concurrently in one step. In step 410, the oral appliance can be contacted with medicament either by the same or another 3D printer head or by applying the medicament to the oral appliance to load it. The porous regions will absorb more medicament than the non-porous regions. The porous regions will allow more medicament release from the oral appliance, while the non-porous regions will allow no or little medicament release from those discrete locations of the oral appliance or confine it to specific regions of the oral appliance. In some embodiments, the oral appliance can have alternating layers of low density porous material and high density non-porous material to provide the desired medicament release from the oral appliance.

Figure 12:
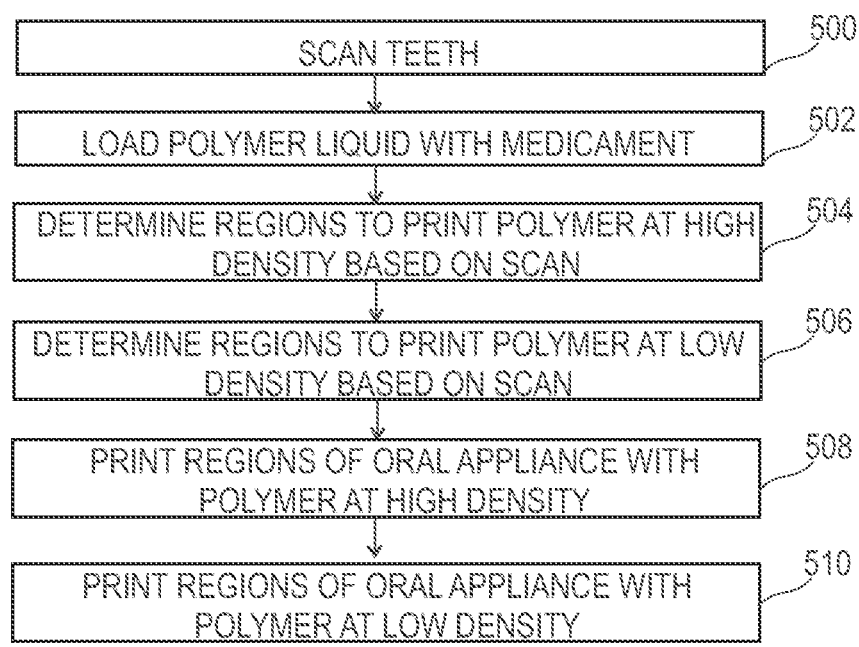
FIG. 12 is a flow chart illustrating one embodiment of the computer-implemented system and steps that the computer performs to produce an oral appliance. The medicament is mixed with one polymer. The oral appliance comprises discrete regions made from porous and non-porous polymer, where the printer density of the polymer is controlled and areas of high density polymer printing are non-porous and areas of low density polymer printing are porous.

FIG. 12 is a flow chart illustrating one embodiment of the computer-implemented system that the computer performs to produce the oral appliance, which is pre-loaded with medicament.

In FIG. 12, when the oral appliance is made by 3D printing, the data from the scan of the teeth in step 500 is reviewed by a practitioner and data is entered into the computer to instruct the printer to print the oral appliance. The polymer containing the medicament used to make the oral appliance is loaded in the printer in step 502 and the area for high density printing (non-porous region) of the oral appliance is determined in step 504. The data from the scan of the teeth in step 500 is reviewed and the area for low density printing (porous region) of the oral appliance is determined in step 506. Data is sent to the printer, which can be instructed by the computer to print the polymer at different densities so that one polymer material can be used to make the oral appliance. The 3D printer can be instructed to print polymer in a high density amount at discrete regions of the oral appliance in step 508 based on the scan, which will be the non-porous region of the oral appliance. The printer can be instructed and will then print a low density amount of polymer on the oral appliance in step 510 based on the scan to make discrete porous regions of the oral appliance. In some embodiments, the high density regions and the low density regions can be printed or manufactured either in separate steps, simultaneously or concurrently in one step. The oral appliance can be removed from the substrate and it will already have the medicament loaded in it.

In some embodiments, the porous material comprises an open cell, lattice or honeycomb configuration, as shown in FIG. 1B. These open cell, lattice, honeycomb or other random or geometric patterned configurations can have different shapes including, for example, regular or irregular polygon including arcuate, round, square, oblong, kidney shaped, crescent, or beveled shaped. In the embodiment shown, the oral appliance can have portions of open cells, lattices or honeycombs as part of the oral appliance at discrete regions of it. The entire oral appliance, the porous material, or discrete regions of the oral appliance includes or is manufactured to include carbon foam, polymer(s), or a combination thereof. The foam can be a carbon foam lattice, such as carbon resin DPR 10 (Carbon 3D, Inc. C.A.). These polymer materials can be printed, for example, by Carbon 3D printers.

The carbon foam, and/or polymer(s), can affect the application and/or release of the medicament. In some embodiments, the entire oral appliance is made from carbon foam or polymer(s), and the density of the carbon foam or polymer(s) vary from very dense regions which create the non-porous regions of the oral appliance, to less dense regions which create the porous regions of the oral appliance. The very dense, non-porous regions prevent the release of the medicament.

The carbon foam or polymer(s) allow the porosity of the oral appliance to be controlled. For example, the oral appliance can be 3D printed with carbon foam or polymer(s) and the areas not including the gum line can be printed densely where there are little to no open cell, lattice or honeycomb configurations present. However, the gum line area will be printed with the carbon foam or polymer(s) in a less dense manner where open cell, lattice or honeycomb configurations are present to allow influx, or allow release of medicament or other substances to the gum line area. In some embodiments, some areas of the oral appliance can be printed virtually as a solid, and other areas of the oral appliance can be printed as a semi-solid.

In some embodiments, when the oral appliance is made by 3D printing and different polymers having a different density are used, the printer can be instructed to print the low density polymer at discrete regions of the oral appliance, which will be the porous region of the oral appliance. The printer can be instructed to print a higher density of polymer on the oral appliance to make discrete non-porous regions of the oral appliance.

Continuous Production of Oral Appliance

Figure 14:
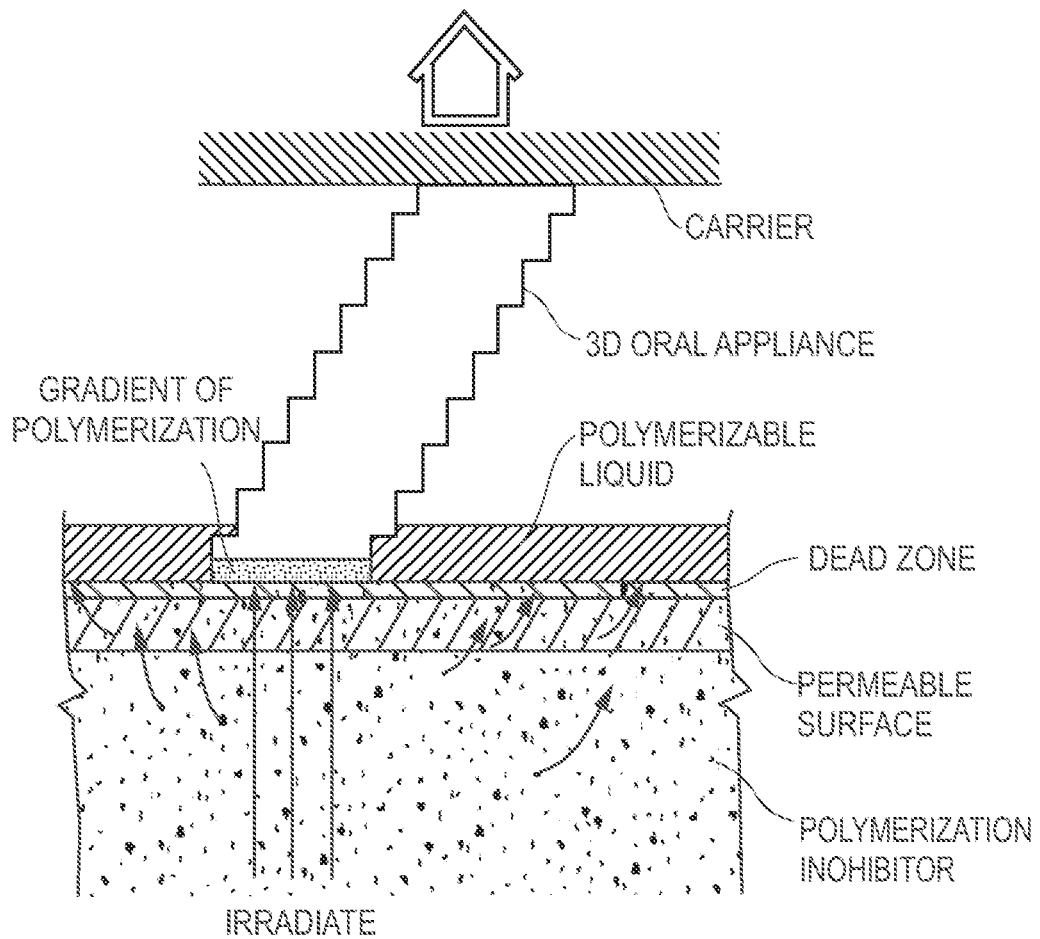
FIG. 14 is a schematic illustration of one embodiment of an apparatus used to make the custom fit oral appliance.

In some embodiments, methods, systems and apparatuses for the generally continuous production of a three-dimensional oral appliance are provided. In these methods, systems and apparatuses, the three-dimensional oral appliance can be produced from a liquid interface, which is often referred to as "continuous liquid interphase printing", suitable methods, systems and apparatuses for making the oral appliance are illustrated in FIG. 14. Suitable operation parameters for the continuous production of the oral appliance using 3D printing technology is described in U.S. Pat. No. 9,205,601 assigned to Carbon3D, Inc. The entire disclosure of this patent is herein incorporated by reference into the present disclosure.

Shown in FIG. 14, the interface is between first and second layers or zones of the same polymerizable liquid. The first layer or zone (sometimes also referred to as a "dead zone") contains an inhibitor of polymerization (at least in a polymerization-inhibiting amount); in the second layer or zone the inhibitor has been consumed (or has not otherwise been incorporated or penetrated therein) to the point where polymerization is no longer substantially inhibited. The first and second zones do not form a strict interface between one another but rather there is a gradient of composition that can also be described as forming an interphase between them as opposed to a sharp interface, as the phases are miscible with one another, and further create a (partially or fully overlapping) gradient of polymerization therebetween (and also between the three dimensional-oral appliance being fabricated, and the build surface through which the polymerizable liquid is irradiated). The three-dimensional oral appliance shown in FIG. 14 can be fabricated, grown or produced continuously from that gradient of polymerization (rather than fabricated layer-by-layer). As a result, the creation of fault or cleavage lines in the oral appliance being produced, which may occur in layer-by-layer techniques may be reduced or obviated. Thus, the oral appliance, in some embodiments, will not have layers or cleavage lines and have a smooth outer surface, which will have the desired non-porous and porous regions (e.g., open cells, lattices, honeycomb, sponge-like configurations, etc.). Of course, such fault or cleavage lines can be intentionally introduced when desired.

Figure 15:
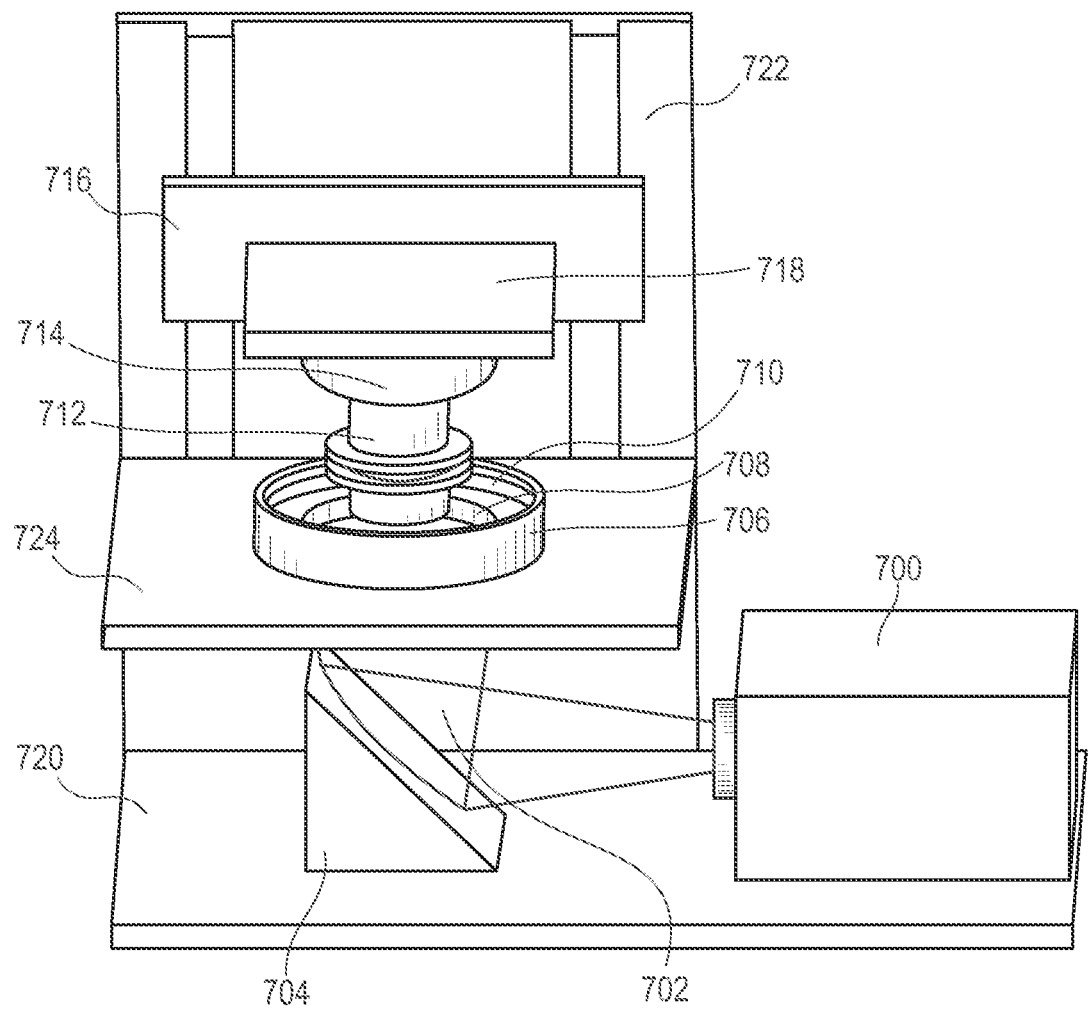
FIG. 15 is a perspective view of one embodiment of an apparatus used to make the custom fit oral appliance.

As shown in FIG. 15, in some embodiments of continuous liquid interphase printing, the first layer or zone is provided immediately on top of, or in contact with, a build plate 708 of an apparatus, as described below. The build plate is transparent to the irradiation which initiates the polymerization (e.g., patterned radiation), but the build plate is, in some embodiments, semipermeable to the polymerization inhibitor and allows the inhibitor of polymerization (e.g., oxygen) to pass partly or fully therethrough (e.g., to continuously feed inhibitor to the "dead zone"). The build plate is, in some embodiments, "fixed" or "stationary" in the sense that it need not slide, retract, rebound or the like to create separate or sequential steps (as in a layer-by layer process). Of course, minor motion of the build plate in the x and/or y directions that does not unduly disrupt the gradient of polymerization, but still permits continuous polymerization from the liquid interface, may still be accommodated in some embodiments.

In some embodiments, the optically transparent member comprises a semipermeable member, and said continuously maintaining a dead zone is carried out by feeding an inhibitor of polymerization through said optically transparent member, thereby creating a gradient of inhibitor in said dead zone and optionally in at least a portion of said gradient of polymerization zone; in other embodiments, the optically transparent member comprises a semipermeable member, and is configured to contain a sufficient amount (or "pool") of inhibitor to continuously maintain the dead zone for a sufficient length of time to produce the oral appliance being fabricated without additional feeding of inhibitor during the process (which "pool" may be replenished or recharged between production runs). In some embodiments, the irradiating step is carried out with a two-dimensional radiation pattern projected into said build region, wherein said pattern varies over time while said concurrently advancing step continues for a time sufficient to form said three-dimensional oral appliance (e.g., during which time said gradient of polymerization zone is maintained).

While the dead zone and the gradient of polymerization zone do not have a strict boundary therebetween (in those locations where the two meet), the thickness of the gradient of polymerization zone is in some embodiments at least as great as the thickness of the dead zone. Thus, in some embodiments, the dead zone has a thickness of from 0.01, 0.1, 1, 2, or 10 microns up to 100, 200 or 400 microns, or more, and/or said gradient of polymerization zone and said dead zone together have a thickness of from 1 or 2 microns up to 400, 600, or 1000 microns, or more. In some embodiments, the gradient of polymerization zone is maintained (while polymerizing steps continue) for a time of at least 5, 10, 15, 20 or 30 seconds, up to 5, 10, 15 or 20 minutes or more, or until completion of the three-dimensional oral appliance.

In some embodiments, the method may further comprise heating said polymerizable liquid as it is supplied to the build region and/or within the build region to reduce the viscosity thereof in the build region. The method may be carried out and the apparatus implemented wherein said carrier has at least one channel formed therein, and said filling step is carried out by passing or forcing said polymerizable liquid into said build region through said at least one channel (e.g., where said carrier has a plurality of channels formed therein, and where different polymerizable liquids are forced through different ones of said plurality of channels; e.g., further comprising concurrently forming at least one, or a plurality of, external feed conduits separate from said oral appliance, each of said at least one feed conduits in fluid communication with a channel in said carrier, to supply at least one, or a plurality of different, polymerizable liquids from said carrier to said build zone).

In some embodiments, the optically transparent member comprises a semipermeable member, and the continuously maintaining a dead zone is carried out by feeding an inhibitor of polymerization through the optically transparent member, thereby creating a gradient of inhibitor in the dead zone and optionally in at least a portion of the gradient of polymerization zone. In some embodiments, the optically transparent member is comprised of a semipermeable fluoropolymer, a rigid gas-permeable polymer, porous glass, or a combination thereof. In some embodiments, the irradiating step is carried out by maskless photolithography.

In some embodiments of the foregoing, the gradient of polymerization zone and the dead zone together have a thickness of from 1 to 1000 microns. In some embodiments of the foregoing, the gradient of polymerization zone is maintained for a time of at least 5 seconds. In some embodiments, the method further comprises the step of disrupting the gradient of polymerization zone for a time sufficient to form a cleavage line in the three-dimensional oral appliance.

In some embodiments, the method further comprises heating the polymerizable liquid to reduce the viscosity thereof in the build region. In some embodiments, the carrier has at least one channel formed therein, and the filling step is carried out by passing or forcing the polymerizable liquid into the build region through the at least one channel.

In some embodiments, the semipermeable member has a thickness of from 0.1 to 100 millimeters; and/or wherein the semipermeable member has a permeability to oxygen of at least $7.5 \times 10^{-17}$ m2s-1 Pa-1 (10 Barrers); and/or wherein the semipermeable member is formed of a semipermeable fluoropolymer, a rigid gas-permeable polymer, porous glass, or a combination thereof. In some embodiments, the irradiating step is carried out with actinic radiation.

In some embodiments, the polymerizable liquid comprises a free radical polymerizable liquid and the inhibitor comprises oxygen. In some embodiments, the polymerizable liquid comprises an acid-catalyzed or cationically polymerizable liquid, and the inhibitor comprises a base. In some embodiments, the build surface is substantially fixed or stationary.

A non-limiting embodiment of an apparatus of the present application is shown in FIG. 15, as described above. It comprises a radiation source 700 such as a digital light processor (DLP) providing electromagnetic radiation 702 which though reflective mirror 704 illuminates a build chamber defined by wall 706 and a rigid build plate 708 forming the bottom of the build chamber, which build chamber is filled with liquid resin 710. The bottom of the chamber is constructed of the rigid build plate comprising a rigid semipermeable member as discussed further below. The top of the oral appliance under construction shown as a simple circle 712 is attached to a carrier 714 (e.g., the carrier described above). The carrier is driven in the vertical direction by linear stage 716, although alternate structures can be used.

Various components of the apparatus are mounted on a support or frame assembly 718. While the particular design of the support or frame assembly is not critical and can assume numerous configurations, in the illustrated embodiment it comprises a base 720 to which the radiation source is securely or rigidly attached, a vertical member 722 to which the linear stage is operatively associated, and a horizontal table 724 to which wall 706 is removably or securely attached (or on which the wall is placed), and with the build plate rigidly fixed, either permanently or removably, to form the build chamber as described above.

Thus, the present application provides a method of making an oral appliance, the method comprising: providing a carrier and an optically transparent member having a build surface, the carrier and the build surface defining a build region therebetween; filling the build region with a polymerizable liquid; irradiating the build region through the optically transparent member to form a solid polymer from the polymerizable liquid while concurrently advancing the carrier away from the build surface to form the oral appliance from the solid polymer, wherein the oral appliance has discrete regions of porous material.

In some embodiments, the polymerizable liquid is irradiated at discrete regions to form the porous material. In some embodiments, the optically transparent member comprises a semipermeable fluoropolymer, a rigid gas-permeable polymer, porous glass, or a combination thereof. In some embodiments, the polymerizable liquid comprises a medicament disposed homogenously throughout the polymerizable liquid.

It is to be understood that the polymerizable liquid is reactive to irradiation such as light (e.g., ultraviolet (UV) light) and the polymerizable liquid can contain photoreactive or photocurable groups for such reactivity to take place. The UV light can be controlled by a computer and the light will irradiate the polymerizable liquid for polymerization. When the polymerizable liquid is irradiated at discrete regions for a longer period of time, the polymerizable liquid forms porous material in the form of open cell, lattice or honeycomb configurations, as shown in FIG. 1B. These porous discrete regions can contain medicament and the medicament will be released from these porous discrete regions. When it is desired for sections of the oral appliance to be non-porous, these sections will be irradiated for a shorter period of time.

Figure 16:
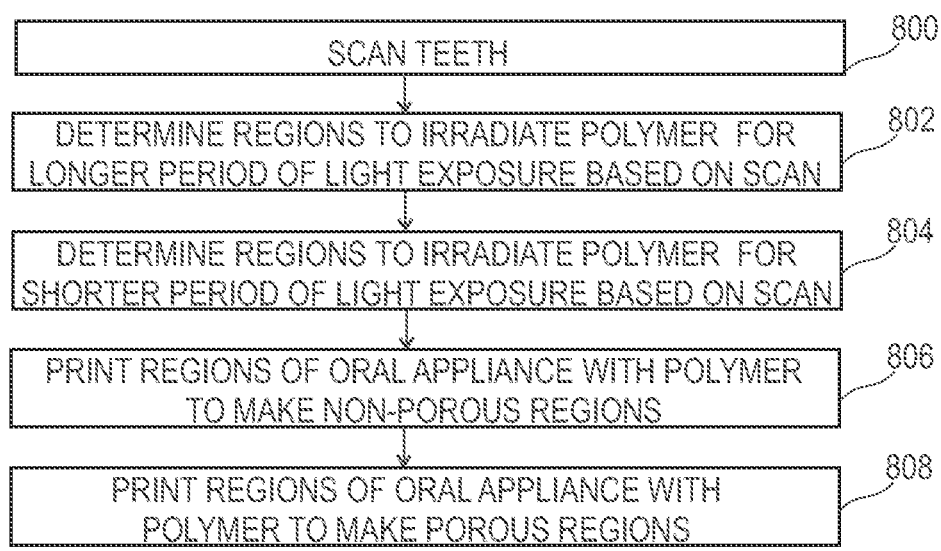
FIG. 16 is a flow chart illustrating one embodiment of the computer-implemented system and steps that the computer performs to produce the oral appliance. The oral appliance comprises discrete regions that are porous and non-porous, and the porous and non-porous regions are made by irradiating these regions with light for a longer or shorter period of time.

FIG. 16 is a flow chart illustrating a computer-implemented system that the computer performs to produce the oral appliance like that shown in FIG. 1B. In FIG. 16, when the oral appliance is made, the data from the scan of the teeth in step 800 is reviewed and regions to irradiate the polymer for a longer period of light exposure based on the scan is determined in step 802. The data from the scan of the teeth in step 800 is reviewed and regions to irradiate the polymer for a shorter period of light exposure based on the scan is determined in step 804. Data is sent to the printer, which can be instructed by the computer to print the regions of the oral appliance with the polymer to make the non-porous regions, as shown in step 806, and to print the regions of the oral appliance with the polymer to make porous regions, as shown in step 808. The regions of the polymer that are irradiated for a longer period of light exposure will become the porous regions, and the regions of the polymer that are irradiated for a shorter period of light exposure will become the non-porous regions. The polymer can be irradiated for a longer period of time, such as, for example, about 25, 30, 35, 40, 45, 50, 55, 60, 65, 70, 75, 80, 85, 90, 95, 100, 105, 110, 115, 120 seconds, or longer. In some embodiments, the polymer can be irradiated for a shorter period time, such as, for example, about 1, 2, 3, 4, 5, 6, 7, 8, 9, 10, 11, 12, 13, 14, 15, 16, 17, 18, 19, or 20 seconds.

Polymerizable Liquids

In some embodiments, a suitable polymerizable liquid can be used to make the oral appliance. The liquid (sometimes also referred to as "liquid resin" "ink," or simply "resin" herein) can include a monomer, particularly photopolymerizable and/or free radical polymerizable monomers, and a suitable initiator such as a free radical initiator, and combinations thereof. Examples include, but are not limited to, acrylics, methacrylics, acrylamides, styrenics, olefins, halogenated olefins, cyclic alkenes, maleic anhydride, alkenes, alkynes, carbon monoxide, functionalized oligomers, multifunctional cute site monomers, functionalized PEGs, etc., including combinations thereof. Examples of liquid resins, monomers and initiators include but are not limited to those set forth in U.S. Pat. Nos. 8,232,043; 8,119,214; 7,935,476; 7,767,728; 7,649,029; WO 2012129968 A1; CN 102715751 A; and JP 2012210408A.

Acid Catalyzed Polymerizable Liquids

While in some embodiments as noted above the polymerizable liquid comprises a free radical polymerizable liquid (in which case an inhibitor may be oxygen), in other embodiments the polymerizable liquid comprises an acid catalyzed, or cationically polymerized, polymerizable liquid. In such embodiments the polymerizable liquid comprises monomers contain groups suitable for acid catalysis, such as epoxide groups, vinyl ether groups, etc. Thus suitable monomers include olefins such as methoxyethene, 4-methoxystyrene, styrene, 2-methylprop-1-ene, 1,3-butadiene, etc.; heterocycloic monomers (including lactones, lactams, and cyclic amines) such as oxirane, thietane, tetrahydrofuran, oxazoline, 1,3, dioxepane, oxetan-2-one, etc., and combinations thereof. A suitable (generally ionic or non-ionic) photoacid generator (PAG) is included in the acid catalyzed polymerizable liquid, examples of which include, but are not limited to onium salts, sulfonium and iodonium salts, etc., such as diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoro arsenate, triphenylsulfonium hexafluoroantimonate, triphenylsulfonium triflate, dibutylnaphthylsulfonium triflate, etc., including mixtures thereof. See, e.g., U.S. Pat. Nos. 7,824,839; 7,550,246; 7,534,844; 6,692,891; 5,374,500; and 5,017,461; see also Photoacid Generator Selection Guide for the electronics industry and energy curable coatings (BASF 2010).

Photocurable Silicone Resins

A suitable resin includes photocurable silicones. UV cure silicone rubber, such as Siliopren™, UV Cure Silicone Rubber can be used as can LOCTITE™ Cure Silicone adhesives sealants. Applications include optical instruments, medical and surgical equipment, exterior lighting and enclosures, electrical connectors/sensors, fiber optics and gaskets.

Biodegradable Resins

Biodegradable resins can be used in making all or portions of the oral appliance. Biodegradable copolymers of lactic acid and glycolic acid (PLGA) can be dissolved in PEG dimethacrylate to yield a transparent resin suitable for use. Polycaprolactone and PLGA oligomers can be functionalized with acrylic or methacrylic groups to allow them to be effective resins for use.

Photocurable Polyurethanes

A particularly useful resin is photocurable polyurethanes. A photopolymerizable polyurethane composition comprising (1) a polyurethane based on an aliphatic diisocyanate, poly(hexamethylene isophthalate glycol) and, optionally, 1,4-butanediol; (2) a polyfunctional acrylic ester; (3) a photoinitiator; and (4) an anti-oxidant, can be formulated so that it provides a hard, abrasion-resistant, and stain-resistant material (U.S. Pat. No. 4,337,130). Photocurable thermoplastic polyurethane elastomers incorporate photoreactive diacetylene diols as chain extenders.

High Performance Resins

In some embodiments, high performance resins are used. Such high performance resins may sometimes require the use of heating to melt and/or reduce the viscosity thereof, as noted above and discussed further below. Examples of such resins include, but are not limited to, resins for those materials sometimes referred to as liquid crystalline polymers of esters, ester-imide, and ester-amide oligomers, as described in U.S. Pat. Nos. 7,507,784; and 6,939,940. Since such resins are sometimes employed as high-temperature thermoset resins, in the present application further comprise a suitable photoinitiator such as benzophenone, anthraquinone, and fluoroenone initiators (including derivatives thereof) to initiate cross-linking on irradiation.

Particularly useful resins for dental applications include EnvisionTEC's Clear Guide, or EnvisionTEC's E-Denstone Material. The liquid resin or polymerizable material can have solid particles (e.g., medicament (e.g., drug or drug-like compounds), sugars, small organic compounds, pigments, dyes, detectable compounds (e.g., fluorescent, phosphorescent, radioactive), etc.) or other material (e.g., proteins, peptides, nucleic acids (DNA, RNA) such as siRNA etc., including combinations thereof suspended or dispersed therein. The particles can be metallic, organic/polymeric, inorganic, or composites or mixtures thereof. The particles can comprise an active agent or detectable compounds, though these may also be provided dissolved solubilized in the liquid resin.

Inhibitors of Polymerization

In manufacturing the oral appliance, in some embodiments, inhibitors of polymerization can be used. More particularly, inhibitors or polymerization inhibitors for use in the present application may be in the form of a liquid or a gas. The specific inhibitor will depend upon the monomer being polymerized and the polymerization reaction. For free radical polymerization monomers, the inhibitor can conveniently be oxygen, which can be provided in the form of a gas such as air, a gas enriched in oxygen (optionally but in some embodiments containing additional inert gases to reduce combustibility thereof), or in some embodiments pure oxygen gas. In alternate embodiments, such as where the monomer is polymerized by photoacid generator initiator, the inhibitor can be a base such as ammonia, trace amines (e.g., methyl amine, ethyl amine, di and trialkyl amines such as dimethyl amine, diethyl amine, trimethyl amine, triethyl amine, etc.), or carbon dioxide, including mixtures or combinations thereof.

While particular embodiments of the present disclosure have been shown and described, it will be appreciated by those skilled in the art that, based upon the teachings herein, changes and modifications may be made without departing from this disclosure and its broader aspects and, therefore, the appended claims are to encompass within their scope all such changes and modifications as are within the true spirit and scope of this disclosure. The true spirit and scope is considered to encompass devices and processes, unless specifically limited to distinguish from known subject matter, which provide equivalent functions as required for interaction with other elements of the claims and the scope is not considered limited to devices and functions currently in existence where future developments may supplant usage of currently available devices and processes yet provide the functioning required for interaction with other claim elements.

What is claimed is:

1. An oral appliance for delivering a medicament to at least a portion of teeth and/or soft tissue areas inside an oral cavity, the oral appliance comprising a porous material containing a medicament to form a porous region and a non-porous material disposed on or in one or more discrete regions of the porous material to form a non-porous region as a structural backbone, the porous region of the oral appliance being formed to fit contours of at least the portion of the teeth and/or soft tissue areas inside the oral cavity and being configured for holding the medicament in contact with at least the portion of the teeth and/or soft tissue areas inside the oral cavity to deliver the medicament thereto, wherein the porous regions are disposed on top of the non-porous region of the interior surface of the structural backbone and the oral appliance does not move teeth.

2. The oral appliance of claim 1, wherein the non-porous material reduces medicament release from the oral appliance.

3. The oral appliance of claim 1, wherein the porous material comprises a polymer.

4. The oral appliance of claim 3, wherein the polymer allows the medicament to be loaded within the polymer.

5. The oral appliance of claim 1, wherein (i) the porous material comprises about 60% to about 99% by weight of the oral appliance; or (ii) the non-porous material comprises about 0.25% to 10% by weight of the oral appliance.

6. The oral appliance of claim 1, wherein the oral appliance has a thickness of from about 0.06 inches to about 0.2 inches.

7. The oral appliance of claim 1, wherein the oral appliance comprises a semi-solid construction.

8. The oral appliance of claim 1, wherein the non-porous material has a higher density than the porous material.

9. The oral appliance of claim 1, wherein the non-porous material and the porous material are the same material but the non-porous material has a higher density than the porous material as the porous material has a lower density.

10. The oral appliance of claim 1, wherein the oral appliance comprises an exterior surface, the exterior surface comprising the porous material containing the medicament and the non-porous material disposed on or in one or more discrete regions of the porous material to make the one or more discrete regions of the oral appliance non-porous.

11. The oral appliance of claim 1, wherein the oral appliance comprises an interior surface, the interior surface comprising the porous material containing the medicament and the non-porous material disposed on or in one or more discrete regions of the porous material to make the one or more discrete regions of the oral appliance non-porous.

* * * * *